(12) United States Patent
Battista

(10) Patent No.: US 11,523,754 B2
(45) Date of Patent: Dec. 13, 2022

(54) DEVICE AND RELATIVE METHOD FOR DETERMINING EXTRAPYRAMIDAL SYMPTOMS, IN PARTICULAR MOTOR SYMPTOMS OF PARKINSON'S DISEASE

(71) Applicant: Luigi Battista, Potenza (IT)

(72) Inventor: Luigi Battista, Potenza (IT)

(*) Notice: Subject to any disclaimer, the term of this patent is extended or adjusted under 35 U.S.C. 154(b) by 301 days.

(21) Appl. No.: 16/492,146

(22) PCT Filed: Mar. 28, 2018

(86) PCT No.: PCT/IB2018/052129
§ 371 (c)(1),
(2) Date: Sep. 8, 2019

(87) PCT Pub. No.: WO2018/178896
PCT Pub. Date: Oct. 4, 2018

(65) Prior Publication Data
US 2021/0128024 A1    May 6, 2021

(30) Foreign Application Priority Data

Mar. 30, 2017 (IT) .................. 102017000035240

(51) Int. Cl.
*A61B 5/00* (2006.01)
*A61B 5/11* (2006.01)

(52) U.S. Cl.
CPC .......... *A61B 5/1121* (2013.01); *A61B 5/1101* (2013.01); *A61B 5/1114* (2013.01); *A61B 5/4082* (2013.01); *A61B 5/681* (2013.01); *A61B 5/7246* (2013.01); *A61B 5/7257* (2013.01); *A61B 2562/0219* (2013.01)

(58) Field of Classification Search
CPC ........ A61B 5/11; A61B 5/1101; A61B 5/4082
See application file for complete search history.

(56) References Cited

U.S. PATENT DOCUMENTS

| 2010/0030119 A1 | 2/2010 | McNames |
| 2013/0041290 A1 | 2/2013 | Kording |
| 2013/0060124 A1* | 3/2013 | Zietsma ............... A61B 5/1101 600/407 |

(Continued)

OTHER PUBLICATIONS

Heida et al., "Power Spectral Density Analysis of Physiological, Rest and Action Tremor in Parkinson's disease patient treated with deep brain stimulation", 2013, Journal of NeuroEngineering and Rehabilitation, 10:30, p. 3 (Year: 2013).*

(Continued)

*Primary Examiner* — Etsub D Berhanu
(74) *Attorney, Agent, or Firm* — Themis Law

(57) ABSTRACT

A method and a related device to determine the kinetic state of a subject includes the steps of determining a signal indicative of the acceleration trend on the three Cartesian axes; processing the signal to limit the frequency band and preferably reduce artifacts and compensate the offset of the output signals from a multi-axial measurement system; analyzing frequency and spectrum through the transformation of the signal with the Fournier transform; computing the power spectral density for each Cartesian axis; and comparing the spectral density with a characteristic pattern of a movement.

14 Claims, 15 Drawing Sheets

(56) References Cited

U.S. PATENT DOCUMENTS

2015/0190085 A1    7/2015   Nathan

OTHER PUBLICATIONS

Griffiths et al. "Automated Assessment of Bradykinesia and Dyskinesia in Parkinson's Disease", 2012, Journal of Parkinson's Disease, p. 2 (Year: 2012).*
Salarian et al., "Quantification of Tremor and Bradykinesia in Parkinson's Disease Using a Novel Ambulatory Monitoring System", Feb. 2007, IEE Transactions on Biomedical Engineering, vol. 54, No. 2, pp. 1-4 (Year: 2007).*
Jorrii Ivar Hoff, Ambulatory accelerometry in Parkinson's disease, Jan. 1, 2005 the whole document.

\* cited by examiner

FIG. 3
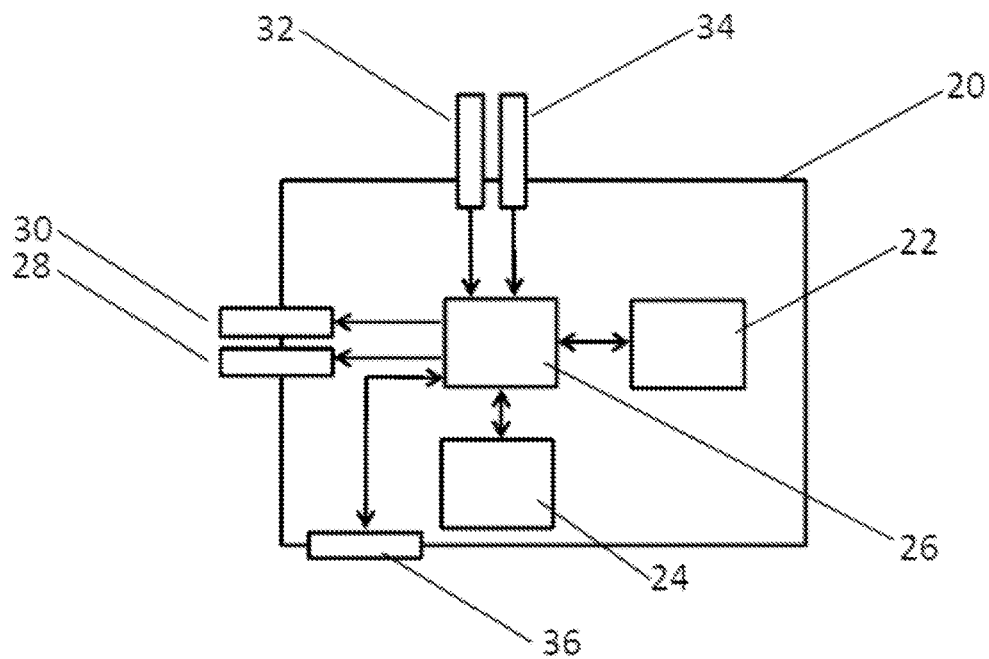
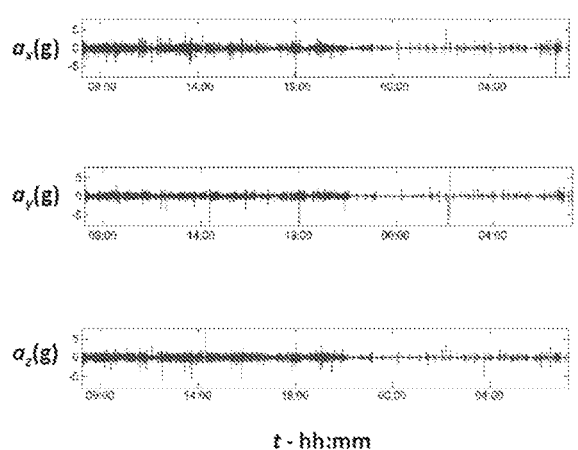
Fig. 4A
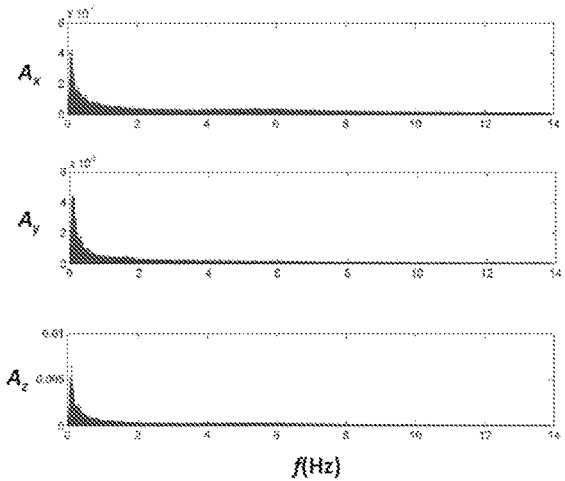
Fig. 4B

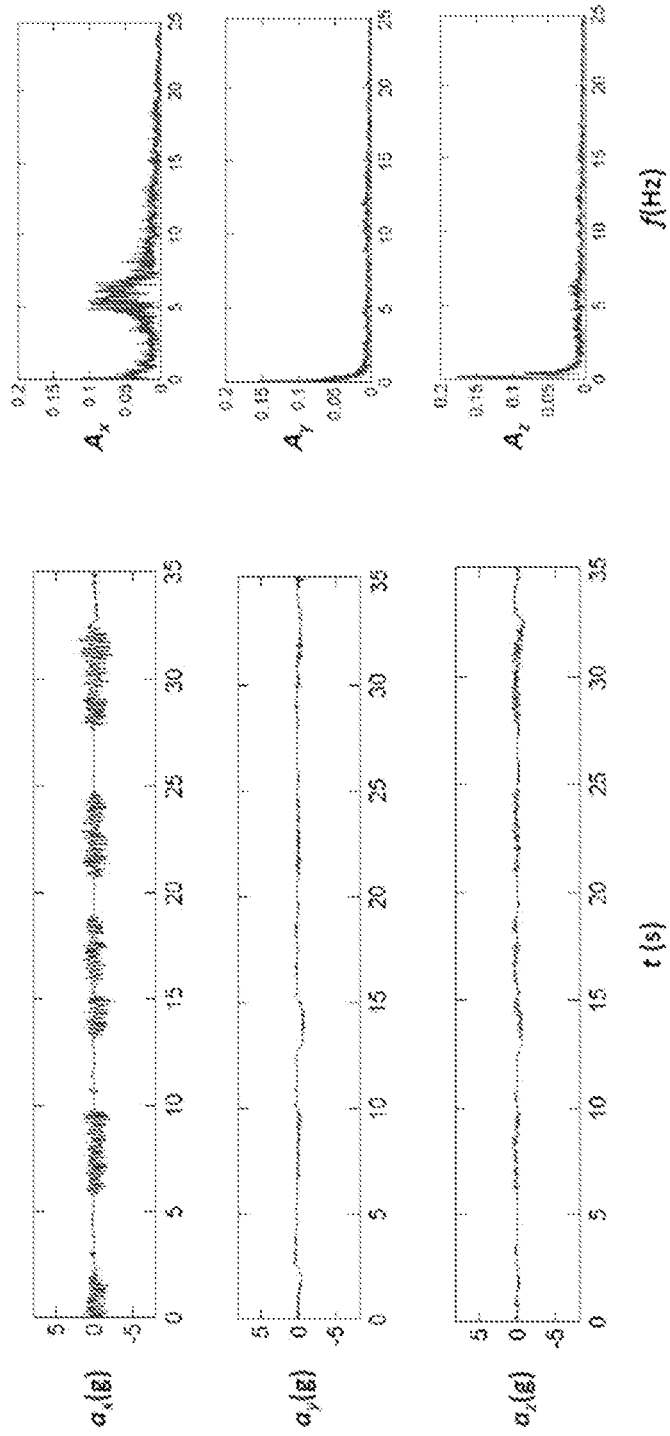

DEVICE AND RELATIVE METHOD FOR DETERMINING EXTRAPYRAMIDAL SYMPTOMS, IN PARTICULAR MOTOR SYMPTOMS OF PARKINSON'S DISEASE

FIELD OF THE INVENTION

The present industrial invention refers to a method and the related apparatuses for the continuous and long-term monitoring of motor symptoms due to Parkinson's disease, Parkinsonism, and extrapyramidal symptoms.

Specifically, the invention refers to an innovative device, and related method, which allows for the continuous monitoring of extrapyramidal symptoms, as well as symptoms related to Parkinson's disease and Parkinsonism, by accurately distinguishing the various motor symptoms from regular activities performed daily by the patient, with the potential to quantify the effects that result from the various motor symptoms.

BACKGROUND INFORMATION

Parkinson's disease is the second most common neurodegenerative disease. It has been estimated that approximately 250,000 patients in Italy, 1.2 million in Europe, and 20 million worldwide are affected by this disease. The mains symptoms of Parkinson's disease are tremor at rest, rigidity, bradykinesia and postural instability. To date, there have been different therapeutic methods available to alleviate symptoms due to Parkinson's disease, including drug treatment, mainly Levodopa, or dopaminergic agonists, and surgical therapy, mainly through deep brain stimulation (Deep Brain Stimulation, DBS), or lesion surgery.

The clinical evaluation of the symptoms of Parkinson's disease is therefore fundamental for the assessment of a patient's health and the efficacy of the ongoing therapeutic treatment; this evaluation is essentially clinical and is typically performed through neurological examinations, motor tests, tests performed in the presence of clinicians, evaluation scales, and daily diaries/reports provided by the patient. However, these tests only allow for the evaluation of the patient's health during the examinations themselves, which are limited in time and cannot detect fluctuations in motor symptoms, and which may vary considerably during the day and from day to day. In addition, evaluation scales and reports are subjective, while neurological visits require the presence of a clinician.

In recent years, several devices have been proposed to more objectively quantify the symptoms of Parkinsonism patients, including the systems reported in U.S. Pat. Nos. 8,187,209 B1, 5,772,611 A, 8,469,884 B2, 4,306,291 A, no. AT411011B and in the patent application no. US20130338539 A1. However, although the devices described in these publications may provide, under certain test conditions, objective ways of measuring Parkinsonism symptoms, they are not always able to provide continuous monitoring of the patient throughout the day.

In addition to the systems mentioned above, method and systems have also been proposed for the continuous and long-term monitoring of Parkinsonism symptoms, which are typically based on the use of wearable sensors: patent No. EP2674104 B1 refers to a method and system able to determine the kinetic state of a person, with the potential to detect bradykinesia and dyskinesia; patent applications no. US20130123666 A1 and no. US20140257141 A1 refer to a movement disorder monitoring system and a method of detecting the relative severity of tremors with the potential for home use; the publication US2010/0030119 is also noted, which regards a system of monitoring movement disorders and appears to be superimposable to the preamble of claim 1.

Many of the aforementioned systems are based on the use of magneto-inertial systems, such as accelerometers and gyroscopes, which are worn by the patient suffering from Parkinson's disease in order to detect the movements of one or more body limbs, wrists, or hands; in most of the proposed methods, the data measured by the measuring devices are processed to perform a frequency analysis and a spectral analysis in the frequency domain. This processing is usually carried out with the aim of quantifying the frequency content in certain frequency ranges, corresponding to those in which Parkinsonism symptoms typically occur. In fact, it is reported in the research that with Parkinson's disease, tremors usually occur between 3 and 7 Hz; dyskinesia may occur, according to various modalities, mainly in the intervals between 1 and 3 Hz, and secondly, in the intervals between 3 and 8 Hz. Moreover, the scientific literature demonstrates that bradykinesia is usually evaluated in an interval whose lower limit is 0.2 Hz and whose upper limit can vary between 4 and 15 Hz, while tremors due to essential tremors are typically evaluated considering an intervals between 3 and 12 Hz and 10 Hz ("J. Janckovic, *Parkinson's disease: clinical features and diagnosis*, Journal of Neurology, Neurosurgery and Psychiatry, 2008, doi:10.1136/jnnp.2007.131045").

Therefore, many of the proposed systems quantify the motor symptoms (in some cases by means of indices, scores, or scores) based on the spectral content and/or the value of the spectral density in the intervals or sub-intervals. However, many common movements, which have nothing to do with Parkinson's disease tremors and other extrapyramidal symptoms, fall in the frequency ranges in which Parkinsonian tremors and other movement disorders typically occur.

Presently, the proposed tests confuse movements that are not due to movement disorders with movements due to Parkinsonism and extrapyramidal symptoms, which creates results that are not entirely accurate. In fact, the routine, daily actions that are typically performed by the patient can affect the frequency range between 0 and 20 Hz, and therefore, may have a frequency content inside the same frequency ranges in which the Parkinsonism motor symptoms occur (M. J. Mathie et al., *Accelerometry providing an integrated practical method for long term ambulatory monitoring of human movement*, Physiological Measurement, 2004, doi: 10.1088/0967-3334/25/2/R01). Therefore, many of these proposed evaluation methods and symptoms do not really distinguish between motor activity due to Parkinsonism and extrapyramidal symptoms, and those from voluntary actions regularly performed by the patient. Moreover, the different Parkinsonism symptoms also have frequent intervals that typically may overlap each other, therefore the mere evaluation of frequency content is not always sufficient when trying to discriminate between one symptom and another.

Ultimately, a simple spectral analysis of the frequencies does not completely solve the technical problems and therefore there is a risk of confounding, with the measurements carried out, normal activity with activity due to the disease.

SUMMARY OF THE INVENTION

The objective of the present invention is therefore to provide an innovative device, and a relative method, which solves the technical problems mentioned above.

Specifically, the objective of the present invention is to provide a device, and a relative method, to carry out the continuous monitoring of the movements to accurately distinguish normal movements from those due to a tremor from Parkinson's disease and extrapyramidal symptoms. These and other objectives are therefore obtained with the present device to determine a motor state of the subject, in accordance with claim 1.

This device comprises:

A multi-axial measuring device (20) to determine at least one signal indicative of the motion of a limb or one or more parts of the body;

A processor programmed to perform a frequency analysis and spectral processing of at least one signal to identify the frequency content of the signal at each axis of the multi-axial measurement system;

In accordance with the invention, this processor is further programmed to perform an analysis at each axis of the frequency content, said analysis comprising the determination of the frequency content of the individual axes to then carry out a verification of compatibility with a reference pattern.

Thanks to this comparison of the frequency content measured on each axis with a reference pattern, it is in this way possible to determine with high accuracy the type of motor state that may be assimilated with motor symptoms and movement disorders of a subject, distinguishing this type of motion with other types of movements, including voluntary movements performed by a subject who, despite having a frequency content similar to that in which movement disorders typically occur, have nothing to do with the effects of neurodegenerative diseases. In this way, the potential to discriminate movement disorders from other natural or voluntary movements allows for the reduction of doubt that arises when the frequency content between these two types of movements are similar but, in reality, the content is determined by a voluntary movement that has nothing to do with a pathological condition.

Advantageously, an optimal solution may provide for a comparison of said frequency contents detected on the individual axes in such a way as to verify, following this inter-axis comparison, if correspondence with a reference pattern exists.

For example, frequency contents with greater values on one axis rather than another may be indicative and typical of predetermined movements (for example pronation-supination), which are in turn indicative of movements related to a certain pathology rather than a natural movement.

These and other objectives are also achieved with the present method for determining the motor state of a subject, in accordance with claim 1.

This method comprises the steps of:

Determination of at least one signal indicative of the motion of a limb or one or more parts of the body with a multi-axial measuring device;

The frequency analysis and spectral processing of at least one signal to identify the frequency content of the signal at each axis of the multi-axial measurement system;

The analysis, at each axis, of the said frequency content and the verification of compatibility with respect to the frequency characteristics of a specific reference motor state.

In essence, this method is based not only on the evaluation of the frequency content of the data measured by the multi-axial sensors in a given time interval, but also on the identification and recognition of specific movement patterns that Parkinsonism symptoms and extrapyramidal are typically associated with. The identification and discrimination of a specific movement pattern associated with an extrapyramidal symptom, which may be carried out using a multi-axial measurement system and by quantifying the way the frequency content may be detected in given intervals of frequency and in given time intervals, is distributed and allocated on the various axes of the multi-axial measuring system.

The motor symptoms associated with Parkinson's disease are characterized not only by specific typical frequencies, but also by patterns of specific movements, and therefore the way in which this frequency contribution is distributed in correspondence with the various axes of the multi-axial measurement system. In fact, research shows that the tremors in Parkinson's disease are typically characterized by a pronation-supination movement between 3 and 7 Hz, while a tremor due to an essential tremor is typically characterized by a flexion-extension movement between 5 and 10 Hz ("J. Janckovic, Parkinson's disease: clinical features and diagnosis, Journal of Neurology, Neurosurgery and Psychiatry, 2008, doi:10.1136/jnnp.2007.131045"). Moreover, the phenomenology of individual patient dyskinesia typically does not tend to change over time ("A. J. Manson et al., An ambulatory dyskinesia monitor, Journal of Neurology, Neurosurgery & Psychiatry, 2000, doi: 10.1136/jnnp.68.2.196").

Therefore, for example, the pronation-supination typical of a Parkinson's disease tremor is characterized not only by the specific typical frequency values, but also by a higher frequency content characteristic on some axes of the multi-axial measurement system rather than on others, as described in the example outlined below.

The present method, therefore, not only analyzes the frequencies on the axes, but also verifies whether this distribution of frequencies is compatible with (or similar to) a reference motion pattern, for example, a pronation-supination pattern, which is typical of a Parkinson's disease tremor. In this way, it is possible to reduce all cases of uncertainty in which the frequencies fall in a range characteristic of tremors caused by Parkinson's disease, but their actual distribution on the axes correspond to different actions (for example, the voluntary fluttering of the hands), which has nothing to do with the involuntary movements typical of tremors due to Parkinson's disease.

Most of the methods available to date, although they are characterized using triaxial measurement systems, are not always based on the evaluation of the frequency content detected on the individual axes and on the comparative evaluation between the frequency contents detected on the individual axes. In fact, the proposed methods often evaluate the frequency content, in a given frequency range of interest, without explicitly referring to the contribution of the individual axes, but instead starting from, for example, the average quadratic value (Root Mean Square, RMS) of the accelerations, rotations, energy, power, and other physical movements detected on the various axes. For example, the calculation of the mean quadratic value condenses, in the case of the triaxial accelerometer, the information coming from the three axes of the measurement system into a single parameter obtained by calculating the square root of the sum of the squares of the values of each axis. Therefore, many of the proposed methods are based on the evaluation of the frequency content without explicitly referring to the contribution of the individual axes, but instead considering the average quadratic value or other parameters, whose computations are based on condensing or synthesising the information coming from the single axes of the measurement system in a single numerical value or parameter, from which it is not possible to evaluate backwards how the detected frequency contribution is distributed and allocated on each axis.

Advantageously, an evaluative step of the frequency content for each axis may be included, as well as the comparison of said values to each other, axis by axis, to check the correspondence with respect to a reference movement pattern.

Advantageously, according to any of the combinations mentioned above, a signal pre-process step may also be included to limit the frequency band and preferably to reduce artifacts and to compensate the offset of the output signals from the multi-axial measuring system.

Advantageously, this operation of frequency analysis and spectral process signal is carried out through the Fourier transform.

Advantageously, according to any combination mentioned above, the analysis of said frequency content may include the quantification of the manner in which the detected frequency content, in given characteristic frequency ranges and in a given time interval, is distributed on the various axes of the multi-axial measurement system by evaluating the frequency content detected on the individual axes and by comparing the characteristic frequency contents detected on the individual axes.

Advantageously, the quantification of the motor states similar to extrapyramidal symptoms is carried out in one of the following ways:

By combining the computation of numerical indices and the qualitative evaluation of the quantitative time-frequency analysis, as the qualitative evaluation is carried out by examining the spectral analyzes, and/or the time-frequency analyzes, and/or the trend over time numerical indices detected, and/or the graphic display of the numerical indices detected;

The representation of the sequence of indices detected at each interval through a cumulative distribution function and/or reordering operation, in ascending or descending order;

The qualitative evaluation of the quantitative time-frequency analysis, providing an indication of how the frequency content is distributed over the entire monitoring sequence; the way in which the frequency content is distributed on the various axes of the measurement system; the frequency of occurrence of motor activities in the frequency content of interest; the presence of motor activity in intervals of frequency adjacent to the characteristic ones used for the calculation of the indices and in other frequency intervals; the intensity of motor activities in the frequency content of interest; and the number of motor activities in the frequency content of interest.

Advantageously, the identification of a motor state similar to a Parkinson's disease tremor is carried out by the combination of the evaluation of characteristic frequency content, which may include, for example, the frequencies included in the interval between 3 and 7 Hz, and the presence of movement patterns due to pronation-supination.

Advantageously, as better described below with reference to the parameters and indices, identifying the presence of motor patterns due to Parkinson's disease tremors may include:

The subdivision into sub-time intervals of the entire monitoring sequence and the computation of the spectral density for each single axis (Sx, Sy and Sz) and on each time sub-interval of the entire monitoring sequence;

The computation, carried out for the individual intervals and for each axis, of the $E_{Px}$, $E_{Py}$ and $E_{Pz}$ parameters by integrating the spectral densities $S_x$, $S_y$ and $S_z$ over the characteristic frequency range;

The identification of the movement patterns due to pronation-supination at the time intervals for which the following three conditions occur:

$$\begin{cases} E_{Px} > E_{Pz} + \sigma_{xz} \\ E_{Px} > E_{Py} + \sigma_{xy} \\ E_{Pz} > E_{Py} + \sigma_{zy} \end{cases}$$

where $\sigma_{xz}$, $\sigma_{xy}$ and $\sigma_{zy}$ are the threshold values.

Advantageously, the said quantification of the magnitude of the motor state similar to Parkinson's disease tremors may also be supported by the computation of one or more numerical indices, including:

The $L_P$ index (lasting index), whose computation includes the evaluation of the total number of time sub-intervals of the monitoring sequence in which the presence of the motor state has been defined;

The $B_P$ (bustle intensity index), which may take the zero value at the time intervals for which the possible presence of pronation-supination patterns has not been identified, and may take, in correspondence with the other time sub-intervals, the value equal to EP, defined as a linear or non-linear combination of the $E_{Px}$, $E_{Py}$ and $E_{Pz}$, values;

The index $B_P^{TOT}$, obtained by adding the value of the BP indices relative to all the sub-intervals of the monitoring sequence;

The index $\overline{B_P}$, whose computation includes the evaluation of the average value of all the $B_P$ values;

The index $BL_P^{TOT} = L_P \cdot B_P^{TOT}$ and the $\overline{BL_P^{TOT}} = L_P \cdot \overline{B_P}$ index;

The $BL_P$ index, obtained by multiplying the index $BL_P^{TOT}$ and/or the index $\overline{BL_P^{TOT}}$ by a coefficient;

The $B_{Px} = E_{Px}$, $B_{Py} = E_{Py}$ e $B_{Pz} = E_{Pz}$ indices, representative of the contribution provided by each axis to the $B_P$ value evaluated on all the axes;

Additional indices obtained based on the $L_P$ index and/or $B_P$ index.

Advantageously, the identification of the motor state similar to an essential tremor is carried out by the combination of the evaluation of a characteristic frequency content, which may include, for example, the frequency values included in the interval between 3 and 12 Hz, and the presence of a movement pattern due to flexion-extension where preferably the identification of the presence of movement patterns due to flexion-extension includes:

The subdivision into time sub-intervals of the entire monitoring sequence and the computation of the spectral density for each single axis ($S_x$, $S_y$ and $S_z$) and on each time sub-interval of the entire monitoring sequence;

The computation, carried out for the individual time intervals and for each axis, of the $E_{Ex}$, $E_{Ey}$ and $E_{Ez}$, parameters by integrating the spectral densities $S_x$, $S_y$ and $S_z$ over the characteristic frequency range;

The identification of movement patterns due to flexion-extension at the temporal sub-intervals for which all the following two conditions occur:

$$\begin{cases} E_{Ez} > E_{Ex} + \delta_{zx} \\ E_{Ey} > E_{Ex} + \delta_{yx} \end{cases}$$

where and $\delta_{zx}$ and $\delta_{yz}$ are threshold values and in which, even more preferably, the identification of movement patterns due to flexion-extension is carried out at the time sub-intervals for which the following conditions occur:

$$E_{Ez} > E_{Ex} + \delta_{zx}$$

Advantageously, the said quantification of the extent of the motor state similar to an essential tremor is supported by the computation of one or more numerical indices, including:

The $L_E$ index, whose computation includes the evaluation of the total number of time sub-intervals of the monitoring sequence in which the presence of this motor state has been identified;

The $B_E$ index, which may take zero value at the time intervals for which the possible presence of flexion-extension has not been identified, and may assume, at other time intervals, the value equal to $E_E$, defined as the linear or non-linear combination of the $E_{Ex}$, $E_{Ey}$ and $E_{Ez}$ parameters;

The $B_E^{TOT}$ index, obtained by adding the value of all the $B_E$ indices related to all the sub-intervals of the monitoring system;

The $\overline{B_E}$ index, whose computation includes the evaluation of the average value of all the $B_E$ values;

The $BL_E^{TOT} = L_E \cdot B_E^{TOT}$ index and the $\overline{BL_E^{TOT}} = L_E \cdot \overline{B_E}$ index;

The $BL_E$ index, obtained by multiplying the $BL_E^{TOT}$ index and/or the $\overline{BL_E^{TOT}}$ index by a coefficient;

The $B_{Ex} = E_{Ey}$, $B_{Ey} = E_{Ey}$ and $B_{Ez} = E_{Ez}$ indexes, representative of the contribution provided by each axis to the value of $B_E$ evaluated on all the axes;

Additional indices obtained based on the $L_E$ and/or $B_E$ index.

Advantageously, the identification, quantification, and comparative evaluation of the motor state similar to dyskinesia includes the evaluation of a characteristic frequency content, which may incorporate the frequencies between 1 and 8 Hz, and the following steps:

The subdivision into time sub-intervals of the entire monitoring sequence and the computation of the spectral density for each single axis ($S_x$, $S_y$ and $S_z$) and on each time sub-interval of the entire monitoring sequence;

The computation, carried out for the individual time intervals for each axis, of the $E_{Dx}$, $E_{Dy}$ and $E_{Dz}$ parameters by integrating the spectral densities $S_x$, $S_y$ and $S_z$ over the characteristic frequency range;

The computation of a $B_D$ index, defined as a linear or non-linear combination of the $E_{Ex}$, $E_{Ey}$ and $E_{Ez}$ parameters, for all the sequence time sub-intervals;

The identification of possible dyskinesia by evaluating the sub-intervals for which the $B_D$ index value is higher than a threshold value;

The quantification of possible dyskinesia by evaluating the value of $B_D$ only for those sub-intervals in which the identification mentioned above was carried out;

The computation of one or more numerical indices, including:

The $L_D$ index, whose computation includes the evaluation of the total number of time sub-intervals of the monitoring sequence in which the presence of the aforementioned motor state has been identified;

The $B_D^{TOT}$ index, obtained by adding the value of all the $B_D$ indices relating to all the sub-intervals of the monitoring sequence;

The $\overline{B_D}$ index, whose computation includes the evaluation of the average value of all the $B_D$ values;

The $BL_D^{TOT} = L_D \cdot B_D^{TOT}$ index and the $\overline{BL_D^{TOT}} = L_D \cdot \overline{B_D}$ index;

The $BL_D$ index, obtained by multiplying the $BL_D^{TOT}$ and/or $\overline{BL_D^{TOT}}$ index by a coefficient;

The indices $B_{Dx} = E_{Dx}$, $B_{Dy} = E_{Dy}$ and $B_{Dz} = E_{Dz}$, representative of the contribution provided by each axis to the $B_D$ value evaluated on all axes;

Additional indices obtained based on the $L_D$ index and/or the $B_D$ index.

Advantageously, the identification and quantification of the motor state similar to dyskinesia are supported and carried out through the qualitative evaluation of the quantitative time-frequency analysis conducted by examining the spectrograms and/or the power densities as a function of time and frequency at the end, to evaluate the entire monitoring sequence, or part of it:

The extent of the frequency content in the range between 1 and 3 Hz and/or in the range between 3 and 8 Hz, with respect to the entire spectral content;

The extent with respect to the frequency in which motor activities occur that have prevalent frequency content in the range of 1 to 3 Hz and/or in the range of 3 to 8 Hz;

The extent of the spectral density value corresponding to the motor activities that have prevalent frequency content in the range between 1 and 3 Hz and/or in the range between 3 and 8 Hz;

The extent of the difference between the value of the spectral density corresponding to the motor activities that have prevalent frequency content in the range between 1 and 3 Hz and/or in the range between 3 and 8 Hz, and the value of the spectral density at the remaining time sub-intervals of the acquisition sequence;

The mode in which the frequency content (corresponding to the motor activities that have prevalent content frequency in the range between 1 to 3 Hz and/or in the range between 3 to 8 Hz) is distributed over this interval.

Advantageously, the identification, quantification, and comparative evaluation of the motor state similar to bradykinesia includes the evaluation of a characteristic frequency content, which may include the frequency values included in the interval between 0.5 and 3 Hz, and the following steps:

The subdivision into time sub-intervals of the entire monitoring sequence and the computation of the spectral density for each single axis ($S_x$, $S_y$ and $S_z$) and on each time sub-interval of the entire monitoring sequence;

The computation, carried out for the individual time sub-intervals for each axis of the $E_{Bx}$, $E_{By}$ and $E_{Bz}$ parameters by integrating the spectral densities $S_x$, $S_y$ and $S_z$ over the characteristic frequency range;

The computation of the $B_B = 1/E_B$ index, where $E_B$ is defined as a linear or non-linear combination of the $E_{Bx}$, $E_{By}$, and $E_{Bz}$ parameters, for all the time sub-intervals of the sequence;

The identification of possible bradykinesia by evaluating the sub-intervals for which the value of the $B_B$ index is higher than a threshold value;

The quantification of possible dyskinesia by evaluating the value of $B_B$ only for those sub-intervals for which the identification process mentioned above was carried out;

The computation of one or more numerical indices, including:

The $L_B$ index, whose computation includes the evaluation of the total number of time sub-intervals of the monitoring sequence in which the presence of the motor state previously mentioned was identified;

The $B_B{}^{TOT}$ index, obtained by adding the value of all the $B_B$ indices relative to all the sub-intervals of the monitoring sequence;

The $\overline{B_B}$ index, whose computation includes the evaluation of the average value of all the $B_B$ values;

The $BL_B{}^{TOT}=L_B \cdot B_B{}^{TOT}$ index and the $\overline{BL_B{}^{TOT}}=L_B \cdot \overline{B_B}$ index;

The $BL_B$ index, obtained by multiplying the $BL_B{}^{TOT}$ index and/or the $\overline{BL_B{}^{TOT}}$ index by a coefficient;

The $B_{Bx}=E_{Bx}$, $B_{By}=E_{By}$, and $B_{Bz}=E_{Bz}$ indices, representative of the contribution provided by each axis to the $B_B$ value assessed on all the axes;

Additional indices obtained based on the $L_B$ index and/or the $B_B$ index.

This method, as described, may therefore be used to precisely determine any movement disorders due to neurodegenerative diseases.

BRIEF DESCRIPTION OF THE DRAWINGS

Other characteristics and advantages of the device and its related measurement method, due to the invention, will be made clearer with the following description of some features, which are provided as non-limited examples, regarding the attached drawings, in which:

FIG. 3 schematically illustrates the structure of the system with respect to the detection and recording of information regarding the movement of body limbs and other parts of a patient's body;

FIG. 4 schematically illustrates the temporal and frequency trends of continuous, 24-hour monitoring, performed with the accelerometric measuring system that is placed on the wrist of a patient affected by Parkinsonian tremors;

FIG. 8 schematically illustrates the temporal and frequency trends of the wrist monitoring device in the case of a Parkinsonian tremor.

FIGS. 13A and 13B illustrate, for each monitoring sequence, the graphic display of the indices in increasing order; FIGS. 13C and 13D illustrate the graphic display of the indices in terms of cumulative distribution function for each monitoring sequence;

FIG. 14 schematically illustrates the graphic display of the power density detected during two different monitoring sequences of a patient with a Parkinsonian tremor.

FIGS. 16A and 16B illustrate, for each monitoring sequence, the graphic display of the indices in increasing order. FIGS. 16C and 16D illustrate, for each monitoring sequence, the graphic display of the indices in terms of the cumulative distribution function;

The measurements, information, and data reported in the invention come from procedures carried out in accordance with the Helsinki Declaration, and consequently, the informed consent of the volunteers involved had been previously acquired.

DETAILED DESCRIPTION OF PREFERRED REALIZATIONS

Figure 1:
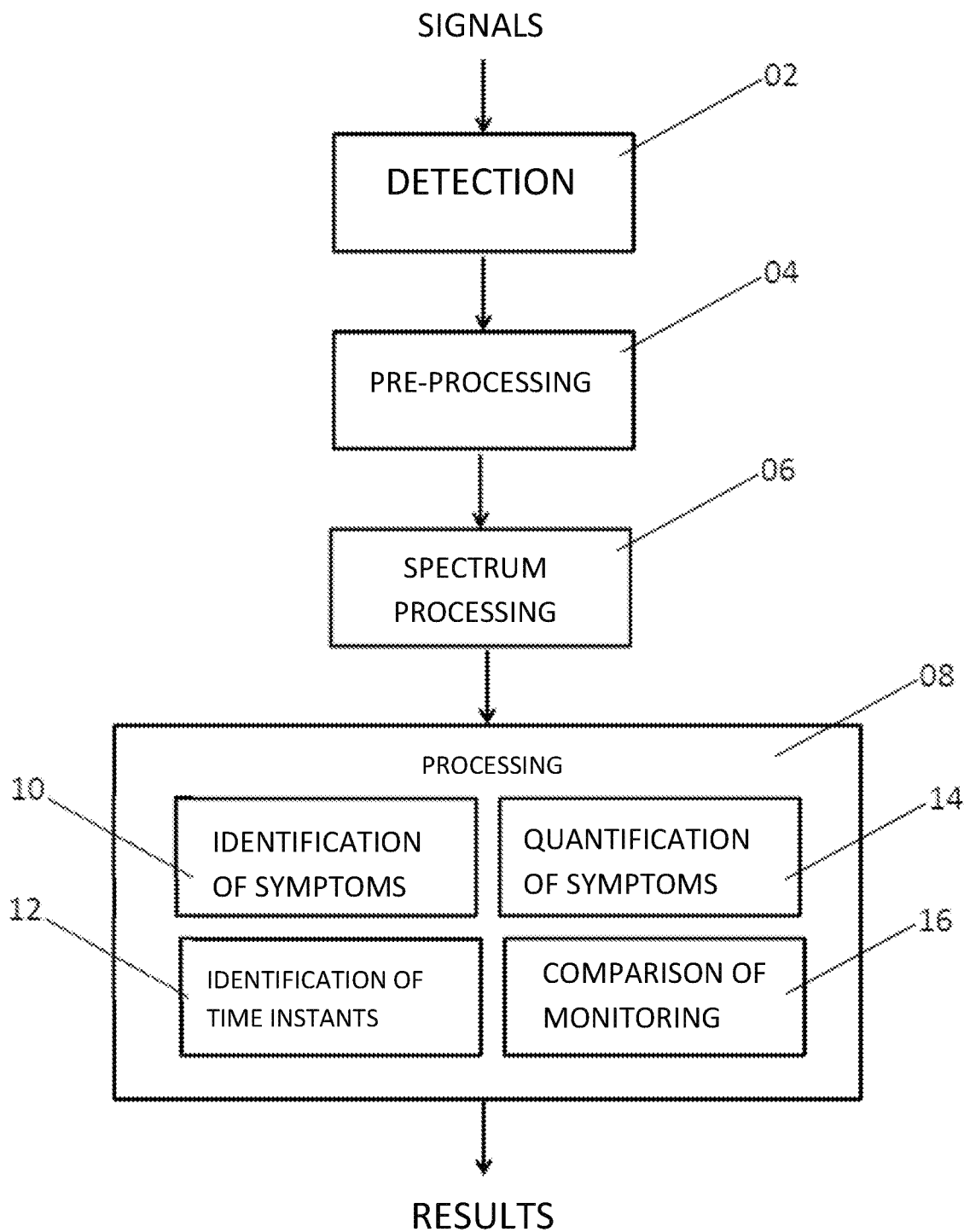
FIG. 1 schematically illustrates the main steps of the identification method, qualitative evaluation, and quantitative evaluation of the extrapyramidal symptoms, according to which the associated device works.

FIG. 1 demonstrates a flowchart that shows the steps to determine a movement, and therefore the kinetic state, of the patient.

Specifically, a method is proposed to identify a motor state to evaluate the presence of possible movement disorders, which includes the following steps:

The detection 02 of signals containing information regarding the movement of body limbs and other parts of the patient's body;

The pre-processing 04 of such signals to limit the frequency band, reduce artifacts, and compensate for the offset of the output signals from the multi-axial measurement system;

The frequency analysis and spectral processing 06 of the signals regarding the identification of the frequency content of the signals being detected and the frequency content detected at each axis of the multi-axial measurement system;

The processing 08 of the signals mentioned above to carry out:

The identification 10 regarding the motor states similar to symptoms due to Parkinson's disease, Parkinsonism, and extrapyramidal symptoms;

The identification 12 regarding the temporal instants in which there are motor states similar to symptoms due to Parkinson's disease, Parkinsonism, and extrapyramidal symptoms;

The quantification 14 regarding the extent of the motor states similar to symptoms due to Parkinson's disease, Parkinsonism, and extrapyramidal symptoms;

The comparative evaluation 16 between monitoring sequences.

The detection 02 of signals containing information regarding the movement of body limbs and other parts of a patient's body continuously takes place over time and through a wearable multi-axial measurement system 20.

Measurements may take place continuously over time, for example, over 24-hours, or durations of 12 or 16 hours may be set to exclude hours of sleep.

Figure 2:
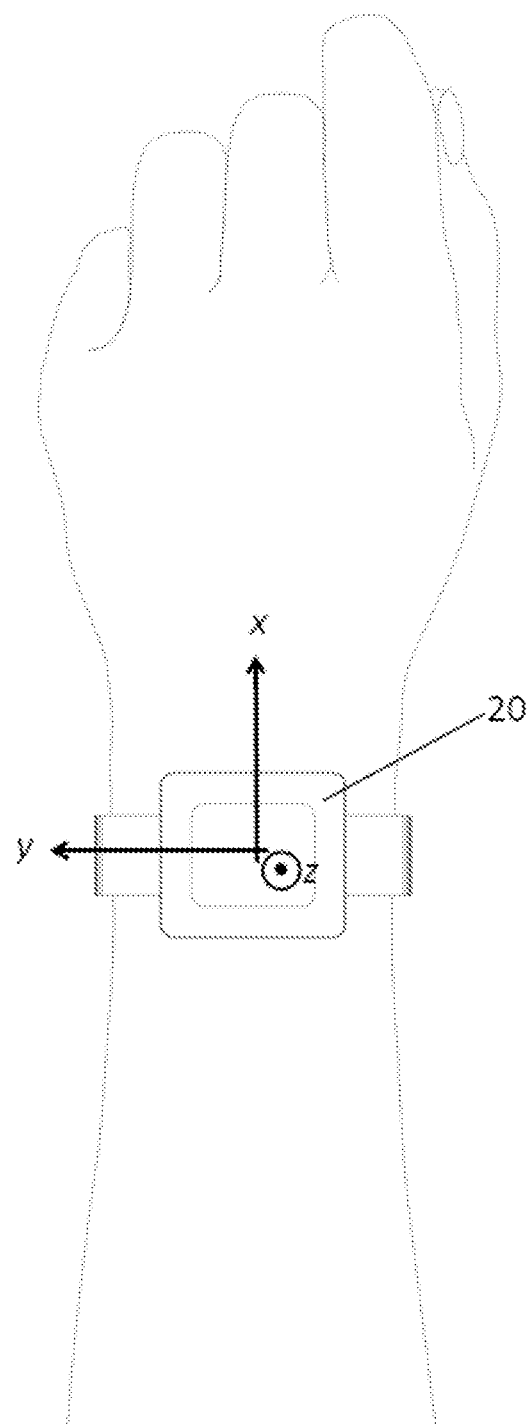
FIG. 2 schematically illustrates the main components of the wearable system with respect to the detection and recording of information regarding the movement of body limbs and other parts of the patient's body.

As shown in FIG. 2, the wearable multi-axial measurement system may consist of a triaxial accelerometer worn on the patient's wrist like a watch. Alternatively, it may be wrapped around another body limb, for example, in the form of a belt or a strap.

FIG. 2 shows the three sample axes (X, Y, Z) and in the most favorable realization, the data coming from each axis of the multi-axial measurement system are sampled at a representative rate of 100 Hz for each axis.

In a possible configuration of the invention, the device 20 of FIG. 2 may therefore contain the following modules or internal devices:

A multi-axial measurement unit for the continuous detection over time of signals containing information on the movement of body limbs and other parts of a patient's body;

A unit to perform the pre-processing of the signals detected by the multi-axial measurement system to limit the frequency band of the signals, reduce the artifacts, and compensate for the offset of the output signals from the multi-axial measurement system;

A unit to perform the spectral processing of the signals provided by the multi-axial measurement system regarding the identification of the frequency content detected at each axis of the multi-axial measurement system;

A unit to carry out the processing of the above signals to:

Identify the presence of motor states similar to symptoms due to Parkinson's disease, Parkinsonism, and extrapyramidal symptoms;

Identify the temporal instants in which there are motor states similar to symptoms due to Parkinson's disease, Parkinsonism, and extrapyramidal symptoms;

Quantify the extent of the motor states similar to symptoms due to Parkinson's disease, Parkinsonism, and extrapyramidal symptoms;

Compare monitoring sequences;

A storage unit that contains the data detected by the multi-axial measurement system;

A storage unit that contains results processed from the previous points;

Communication interfaces (based on wired and/or wireless units) to transfer and/or display the measured and processed information;

Output devices to communicate a reminder and/or the state of the apparatus and/or the power supply system to the patient;

Input devices to communicate a given event (for example, the successful ingestion of a drug, or the occurrence of an odd symptom, such as a very intense tremor).

The integration of such units within a single device 20 that is wearable, such as a watch or a bracelet, may create great bulk and weight. Although this solution is adoptable, as one variation of the invention, the wearable device may be limited to contain only the multi-axial measurement and internal storage unit, while the remaining units that process this information are external.

In this case, the wearable device provides a memory unit so that the triaxial measurement data may be stored and then transferred, through a cable or wirelessly, to the external processing system.

In this regard, FIG. 3 best illustrates the solution in which the wearable device consists internally of the measurement and processing system, while the measurement data is processed externally. Specifically, the processing data for the identification, qualitative and quantitative evaluation of motor states similar to extrapyramidal symptoms occurs externally.

The apparatus in FIG. 3 therefore includes:

A triaxial accelerometer 22 to continuously detect signals containing information regarding the movement of body limbs and other parts of a patient's body over time;

A storage unit 24 for memorizing the data detected by the multi-axial measurement system;

Communication interfaces 36 (based on wired and/or wireless units) to transfer and/or display the measured and processed information;

Output devices to communicate a reminder and/or the state of the apparatus and/or the power supply system to the patient;

Input devices to communicate a given event (for example, the successful ingestion of a drug, or the occurrence of an odd symptom, such as a very intense tremor).

In addition, the system 20 includes the microcontroller 26; the triaxial accelerometer 22 may, for example, be of the Analog Device type ADXL345; the storage unit 24 may, for example, be of the NAND Flash memory type Micron Technology MT29F4G08ABAEAWP:E and a micro-SD memory unit.

The power supply system is a rechargeable battery. The output devices may consist of acoustic and/or visual indicators (for example, 28 and 30 LEDs) that may be used to visualize the results, which provides a reminder regarding the intake of medicine or pharmaceuticals, to indicate the status of the device (for example, a recording in progress, standby, etc.) and/or the status of the power supply system (for example, battery charging/charged, low battery, etc.). The input devices may be made up of one or more switches or buttons (32,34) that may be used to: indicate the successful ingestion of medication or pharmaceuticals; indicate the occurrence of a specific event; request the status of the device or the status of the power supply system; delete the contents of the storage unit; and, to start a new recording. The communication interfaces may include the means necessary to guarantee a wired communication system according to the USB protocol and/or a wired communication according to Bluetooth standards. Moreover, notwithstanding what has been described up until now, in a further variant, the measurement system may include an apparatus for detecting if such a device is worn by the patient or if a motor activity is detected below a certain threshold. In one realization, the apparatus may include a thermometer, a switch, or a heartbeat detector. In one realization, the pre-processing of the signals 04 may include the computation of a $T_{AR}$ index using the previously mentioned apparatus to quantify the temporal duration, during the monitoring, for which an activity value lower than a pre-established threshold occurs.

This system illustrated in FIG. 3 is therefore identical to that of FIG. 2, expect that it may interface with an external processing unit that allows for the identification of motor states similar to extrapyramidal symptoms, as well as the qualitative and quantitative evaluation of the symptoms. In this case, therefore, the external unit comprises:

Communication interfaces (based on wired and/or wireless units) that communicate with the apparatus 20 to detect and record body movements;

A unit to perform the pre-processing of the signals detected by the multi-axial measurement system to limit the frequency band of the signals, reduce the artifacts, and compensate the offset of the output of the multi-axial system;

A unit that carries out the spectral processing of the signals provided by the multi-axial measurement system for the identification of the frequency content detected at each axis of the multi-axial measurement system;

A unit to carry out the processing of the above signals to:

Identify the presence of motor states similar to symptoms due to Parkinson's disease, Parkinsonism, and extrapyramidal symptoms;

Identify the temporal instants in which there are motor states similar to symptoms due to Parkinson's disease, Parkinsonism, and extrapyramidal symptoms;

Quantify the extent of the motor states symptoms due to Parkinson's disease, Parkinsonism, and extrapyramidal symptoms;

Compare monitoring sequences;

A storage unit that contains the data detected by the multi-axial measurement system;

A storage unit that contains the results processed according to the previous points;

Communication interfaces (based on wired and/or wireless units) to transfer and/or display the measured and processed information.

The external processing system for the identification, qualitative evaluation, and quantitative evaluation of the motor states similar to extrapyramidal symptoms may therefore be made up of a "general purpose" computer that may include:

A graphic user interface (GUI) to communicate with the apparatus 20 for the detection and recording of body movements to receive the stored data, recharge the battery, view the battery's status and/or the device, define the parameters of the recording settings, including the start of a recording, sampling frequency, and the duration of a recording;

A source code and/or software application to perform data processing according to the method described in the various forms described above.

In a further variant, the external processing system for the identification, qualitative assessment, and quantitative evaluation of motor states similar to extrapyramidal symptoms may be based on the cloud computing paradigm for storing, processing, and transmitting data. In this case, the data is transmitted, for example through an internet network, to a dedicated processing center.

That said, the innovative part of the present invention relates to the processing mode of data obtained from multi-axial systems to accurately determine movements due to Parkinson's disease and movement disorders.

In a preferred embodiment of the invention, therefore, a device for the determination of a motor state of a subject is provided and it comprises:

A multi-axial measuring device (20) to determine at least one signal indicative of the motion of a limb or one or more parts of the body;

A processor programmed to perform a frequency analysis and spectral processing of at least one signal to identify the frequency content of the signal at each axis of the multi-axial measurement system;

According to the invention, the said processor is further programmed to perform an analysis at each axis, of this frequency content, of this analysis, comprising of a comparison between them of the said frequency contents detected on the individual axes in a way that extrapolates any eventual correspondence with a reference pattern.

Specifically, with reference to FIGS. 4 and 5, trends are reported such as the function of time t, and of trends such as a function of frequency f respectively referring to a patient affected by Parkinsonian tremors and a patient affected by dyskinesia induced by Levodopa.

Figures 5A, 5B:
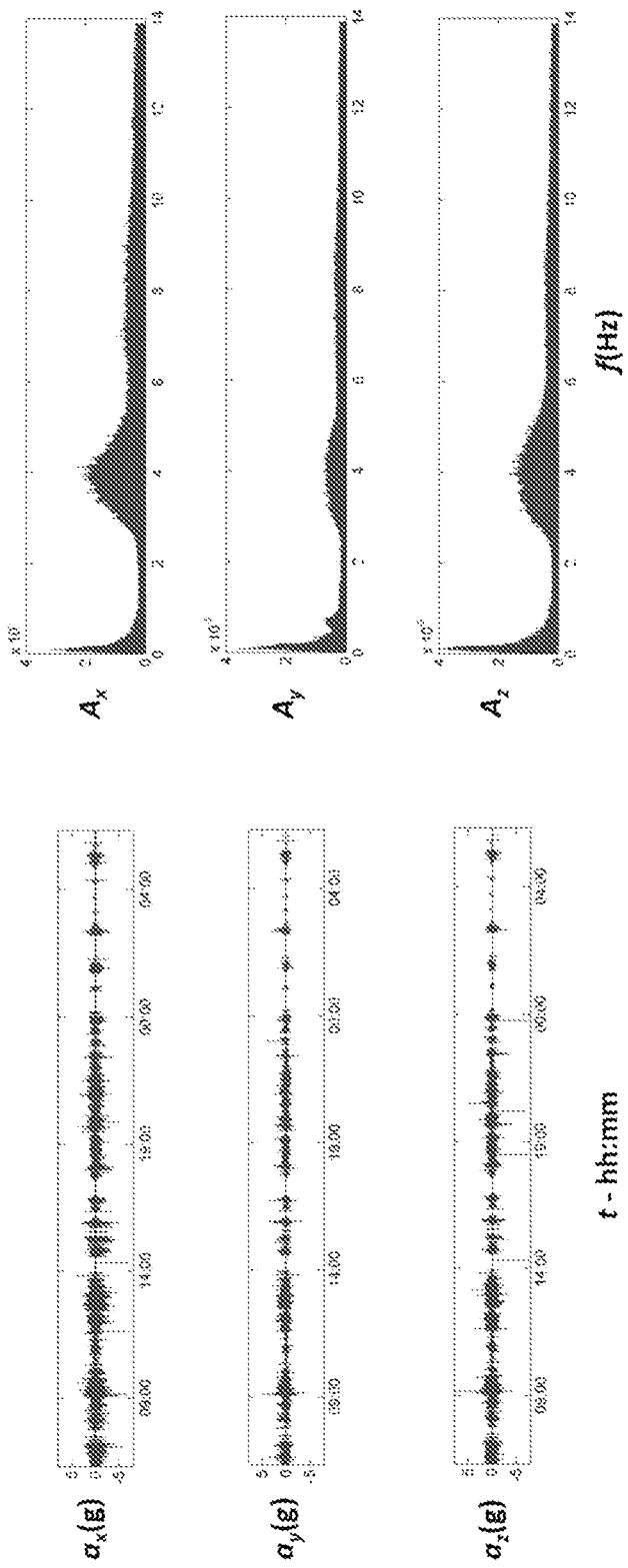
FIG. 5 schematically illustrates the temporal and frequency trends of continuous, 24-hour monitoring, performed with the accelerometric measuring system that is placed on the wrist of a patient affected by levodopa-induced dyskinesia.

FIGS. 4A and 5A show, for each of the three axes (x, y and z), the temporal acceleration trends ($a_x$, $a_y$ and $a_z$) detected by the triaxial accelerometric measuring system 22 that is worn on the wrist of the limb most affected by movement disorders due to Parkinson's disease. These trends are obtained by carrying out continuous monitoring over time, with a sampling frequency of 100 Hz for each axis, and for a duration of 24 hours.

The trends shown in FIGS. 4A and 5A were obtained by the pre-processing process 04.

In one realization, the pre-processing signal 04 may include the use of a band-pass filter to limit the frequency band to reduce the frequency contribution due to the continuous component (up to about 0.2 Hz) and the higher frequencies typically verified during voluntary movement and extrapyramidal symptoms.

In another realization, in addition to or as an alternative to the previous one, the pre-processing signal 04 may include the use of a smoothing filter to compensate for the offset of the output signals from the multi-axial measurement system. In the most favorable realization, the smoothing filter is an average moving filter.

In another realization, the pre-processing signal 04 may include the computation of the average quadratic value of the acceleration:

$$a_{RMS} = \sqrt{\frac{a_x^2 + a_y^2 + a_z^2}{3}} \tag{1}$$

At this point, the signals subject to pre-processing 04 may be subject to spectral processing 06 to identify the frequency content of the signals being detected 02 to identify the frequency content at each axis of the multi-axial measurement system.

According to a possible solution, the frequency processing and the spectral processing 06 may be carried out by calculating the Fourier transform of the detected signal and subject to the pre-elaboration 04. FIGS. 4B and 5B show, in correspondence with each axis, the Fourier transform ($A_x$, $A_y$ and $A_z$) of the signals respectively shown in FIGS. 4A and 5A; these Fourier transforms have been calculated considering the entire duration of the monitoring period, which, in FIGS. 4A and 5A, are equal to 24 hours. From the analysis of the graphs regarding the Fourier transforms reported in FIGS. 4B and 5B, it is possible to verify the extent of the frequency contributions of those frequency ranges in which the extrapyramidal symptoms typically occur. In fact, in FIG. 5B, an important frequency content for frequencies around 4 Hz is evident on all three axes. In FIG. 4B, a frequency contribution around 5 Hz is instead slightly higher than the other frequencies in which the extrapyramidal symptoms typically occur: FIG. 4B shows that this contribution, which is approximately 5 Hz, is more noticeable on the X and Z axes, rather than on the Y axis. However, the examination of the Fourier transform evaluated considering the entire duration of the 24-hour monitoring period, does not permit the evaluation of the time intervals of monitoring at which the presence of such frequency content has occurred, without thereby providing the opportunity to know whether extrapyramidal symptoms have occurred, or any time instances in which such symptoms may have occurred. Therefore, in another realization, in addition to, or as an alternative to the previous ones, the spectral processing 06 may include subdivision into time sub-intervals of the entire monitoring sequence and the computation of the Fourier transform for each individual axis and on each time sub-interval for the entire monitoring sequence.

In one embodiment, the monitoring sequence of each axis may be divided into time sub-intervals, of a duration Δt between 1 second and 10 minutes, for each of which the Fourier transform is computed. In the preferred embodiment, the monitoring sequence may be divided into time sub-intervals, of equal duration, from 4 seconds to 5 minutes, as the sub-intervals of the entire sequence, temporally synchronized for each axis of the triaxial accelerometer. Therefore, in this realization, time sub-intervals of the same duration may be defined, each characterized by a start time and an end time; on each of these sub-intervals that make up the entire monitoring sequence, the Fourier transform is computed on each spatial axis.

In another embodiment, the spectral analysis of each sub-interval may include the use of the Fournier transform computation to perform a time-frequency analysis. This analysis may be performed by identifying the spectral density, power spectral density (Power Spectral Density, PSD), energy spectral density (Energy Spectral Density, ESD), acceleration spectral density (Acceleration Spectral Density, ASD), and other characteristic parameters deriving from the computation of the Fournier transform.

In the preferred embodiment, the spectral analysis of each sub-interval may include, for each axis, the computation of the power spectral density on each sub-interval and for each axis ($S_x$, $S_y$, $S_z$).

In another realization, the time-frequency analysis performed on each sub-interval through the evaluation of the power spectral density for each axis may be visualized by means of a three-dimensional graph. In another realization, the time-frequency analysis performed on each sub-interval through the evaluation of the power spectral density for each axis may be visualized by an image with a spectrographic representation; in another realization, the time-frequency analysis performed on each sub-interval through the e valuation of the power spectral density of the mean quadratic value, calculated considering all the axes, may be visualized by an image with a spectrographic representation.

Figure 6:
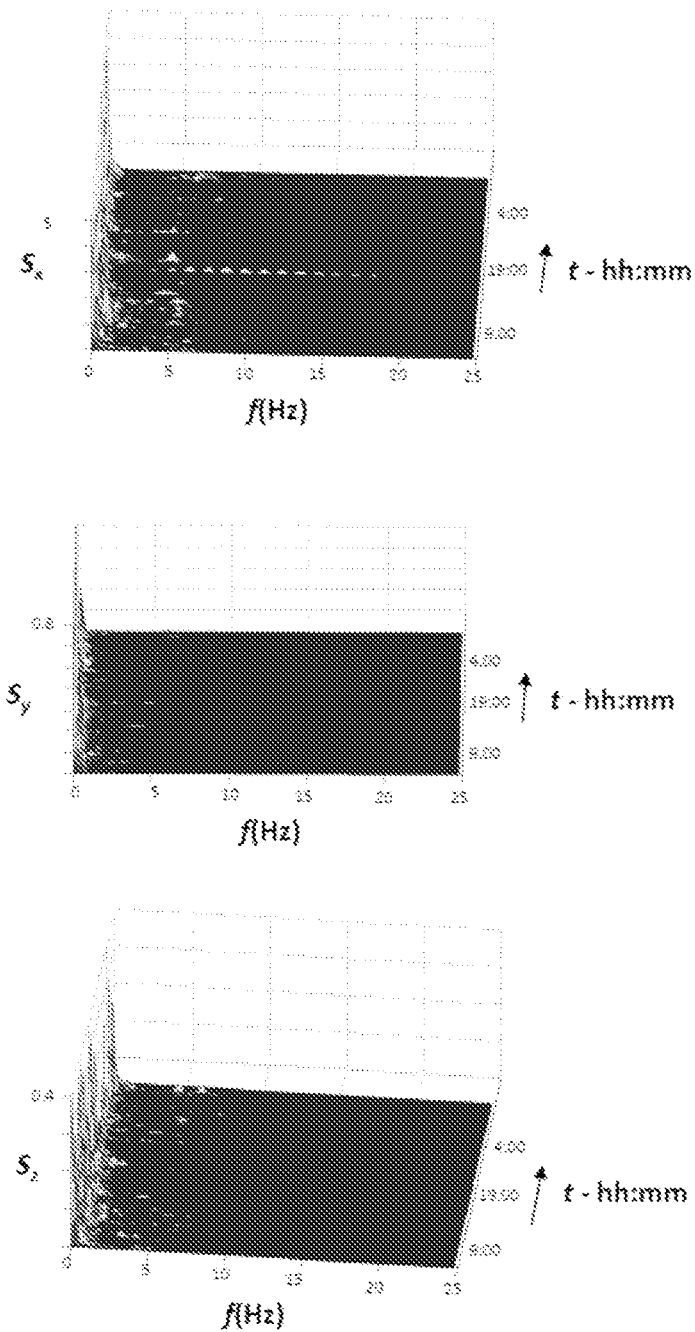
FIG. 6 illustrates, for each axis, the power spectral density as a function of time and the frequency of temporal trends that are shown in FIG. 4A.
Figure 7:
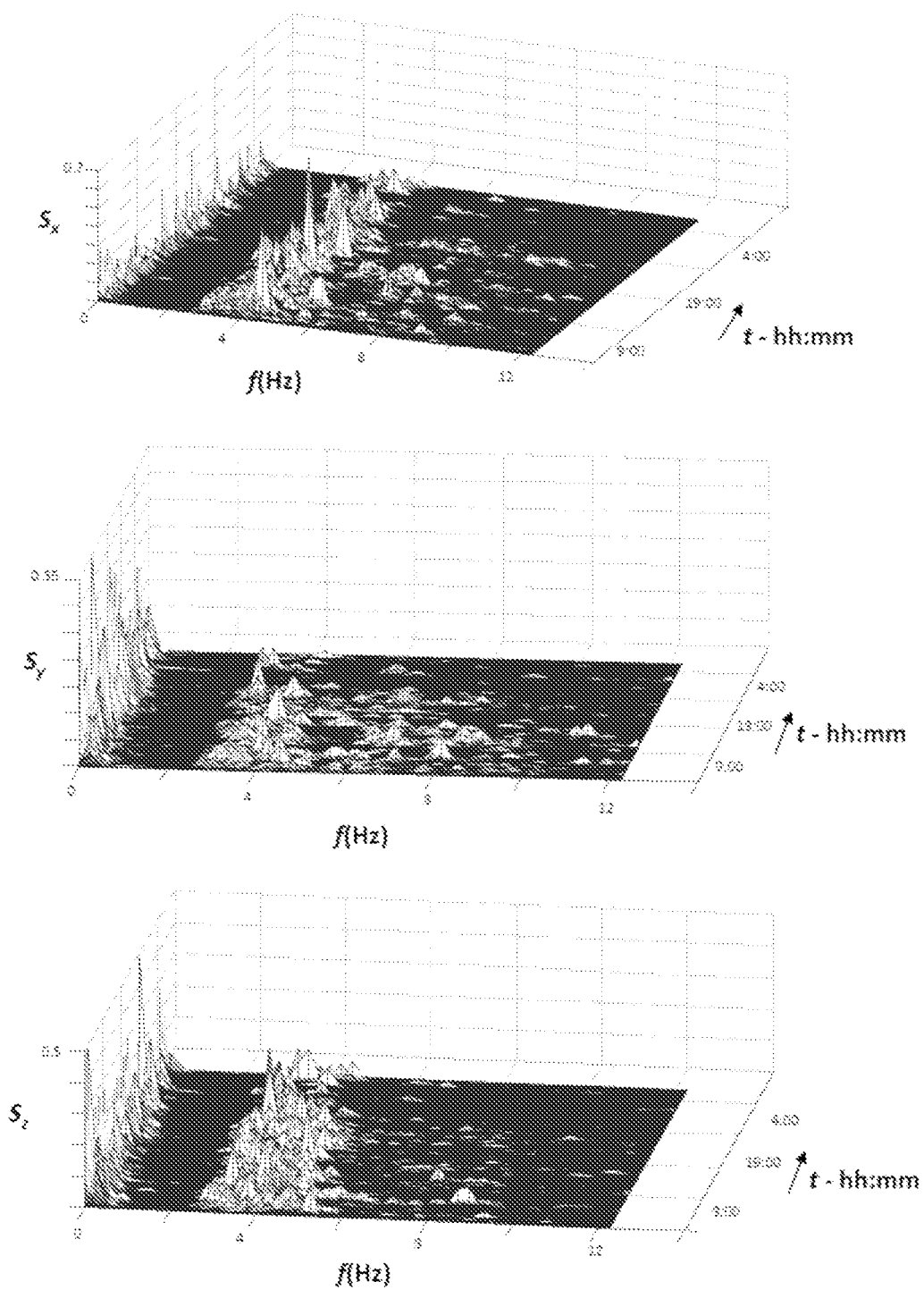
FIG. 7 schematically illustrates, for each axis, the power spectral density as a function of time and the frequency of the temporal trends that are shown in FIG. 5A.

FIGS. 6 and 7 show, for each axis, three-dimensional graphs with the time-frequency analysis calculated by means of spectral power density of the signals, which are respectively reported in FIGS. 4A and 5A; the power spectral density is evaluated on each sub-interval and for each spatial axis of the measurement system. This analysis was carried out by considering equal-duration and synchronous sub-intervals between one axis and another (i.e. the entire monitoring sequence was subdivided into sub-intervals of equal duration and for each sub-interval, characterized by a start time and end time instant, the Fourier transform was computed for each spatial axis).

FIG. 6 shows that there are various moments of the day in which an important frequency content is evident in the intervals in which Parkinsonism symptoms typically occur. Specifically, it is possible to detect a greater number of events with a frequency content between 3 and 7 Hz (interval in which a Parkinsonian tremor typically occurs) in the first part of the monitoring sequence compared to the second part of the monitoring sequence. FIG. 7 shows the presence of multiple and frequent events with a frequency content typically between 2.5 and 9 Hz (the interval in which dyskinesia induced by Levodopa typically occurs).

In another realization, in addition to, or as an alternative to the previous ones, the spectral processing 06 may include the computation, evaluated for the individual time intervals and for each axis, of the spectral energy of the accelerometric signals evaluated in the frequency intervals in which extrapyramidal symptoms typically occur; in one realization, the spectral processing 06 may include the computation, evaluated for the individual time intervals and for each axis, of the spectral content by integrating the spectral densities $S_x$, $S_y$ and $S_z$ considering the frequency ranges where extrapyramidal symptoms are typically checked for. In one realization, the spectral processing 06 may include the computation, evaluated for the individual time intervals and for each axis, of the spectral content through the integration of the spectral densities $S_x$, $S_y$ and $S_z$:

Between 3 and 7 Hz, i.e. the interval in which Parkinsonian tremors typically occur, obtaining the $E_{Px}$, $E_{Py}$ and $E_{Pz}$ parameters;

Between 3 and 12 Hz, i.e. the interval in which essential tremors typically occur, obtaining the $E_{Ex}$, $E_{Ey}$ and $E_{Ez}$ parameters;

Between 1 and 8 Hz, i.e. the interval in which dyskinesia typically occurs, obtaining the $E_{Dx}$, $E_{Dy}$ and $E_{Dz}$ parameters;

Between 0.2 and 3 Hz, i.e. the interval in which bradykinesia is typically evaluated, obtaining the $E_{Bx}$, $E_{By}$ and $E_{Bz}$ parameters.

In another realization, the spectral processing 06 may include the computation of the $E_{Px}$, $E_{Py}$, $E_{Pz}$, $E_{Ex}$, $E_{Ey}$, $E_{Ez}$, $E_{Dx}$, $E_{Dy}$, $E_{Dz}$, $E_{Bx}$, $E_{By}$, $E_{Bz}$ parameters by integrating the spectral densities $S_x$, $S_y$ and $S_z$ on different frequency intervals compared to those indicated above.

In another realization, the spectral processing 06 may include the computation of the $E_P$, $E_E$, $E_D$ and $E_B$ parameters by the linear combination of the axial values:

$$E_P = a_{Px} \cdot E_{Px} + a_{Py} \cdot E_{Py} + a_{Pz} \cdot R_{Pz}$$

$$E_E = a_{Ex} \cdot E_{Ex} + a_{Ey} \cdot E_{Ey} + a_{Ez} \cdot E_{Ez}$$

$$E_D = a_{Dx} \cdot E_{Dx} + a_{Dy} \cdot E_{Dy} + a_{Dz} \cdot E_{Dz}$$

$$E_B = a_{Bx} \cdot E_{Bx} + a_{By} \cdot E_{By} + a_{Bz} \cdot E_{Bz} \quad (2)$$

where the parameters $a_{Px}$, $a_{Py}$, $a_{Pz}$, $a_{Ex}$, $a_{Ey}$, $a_{Ez}$, $a_{Dx}$, $a_{Dy}$, $a_{Dz}$, $a_{Bx}$, $a_{By}$, $a_{Bz}$ are constants. In one realization, the values of these constants are as follows:

$$a_{Px} = a_{Py} = a_{Pz} = a_{Ex} = a_{Ey} = a_{Ez} = a_{Dx} = a_{Dy} = a_{Dz} = a_{Bx} = a_{By} = a_{Bz} = 1 \quad (3)$$

In one realization, the spectral processing 06 may include, for each sub-interval, the computation of the Fourier transform of the mean quadratic value of the $a_{RMS}$ acceleration. In another realization, the spectral processing 06 may include, for each sub-interval, the computation of the $S_{RMS}$ spectral density of the mean quadratic value of the $a_{RMS}$ acceleration.

In one realization, the spectral processing 06 may include the computation, evaluated for the individual time intervals, of the spectral content through the integration of the $S_{RMS}$ spectral density:

Between 3 and 7 Hz, i.e. the interval in which Parkinsonian tremors typically occur, obtaining the $E_{P,RMS}$ parameters;

Between 3 and 12 Hz, i.e. the interval in which essential tremors typically occur, obtaining the $E_{E,RMS}$ parameters;

Between 1 and 8 Hz, i.e. the interval in which dyskinesia typically occurs, obtaining the $E_{D,RMS}$ parameters;

Between 0.2 and 4 Hz, i.e. the interval in which bradykinesia is typically evaluated, obtaining the $E_{B,RMS}$ parameters.

In another realization, the spectral processing 06 may include the normalized computation of the above parameters. By way of example, but not limitation, the following normalized patterns are reported:

$$E_{Px}^{rel} = \frac{E_{Px}}{E_{P,MAX}}, E_{Py}^{rel} = \frac{E_{Py}}{E_{P,MAX}}, E_{Pz}^{rel} = \frac{E_{Pz}}{E_{P,MAX}} \qquad (4)$$

where $E_{P,MAX}$, represents the maximum value of all the $E_{Px}$, $E_{Py}$, $E_{Pz}$ values, considering all the time intervals in which the entire duration of the monitoring is considered. Similarly, the spectral processing 06 may include the normalized computation of the other previously defined parameters (e.g. $E_E$, $E_D$, $E_B$, . . . ).

However, the mere analysis of time-frequency, detection of the parameters indicated above (e.g. $E_P$, $E_E$, $E_D$, $E_B$, . . . ), and the detection of certain frequency contributions in the intervals in which the extrapyramidal symptoms typically occur do not always allow for the effective discrimination between the type of movements that determine the aforementioned frequency contents and, therefore, do not allow the affirmation that the said motor activity was due to an extrapyramidal symptom rather than a voluntary action. Moreover, if this activity is due to an extrapyramidal symptom, it is not always possible to identify which extrapyramidal symptom is the cause, since these symptoms have typical frequency intervals that may overlap one another.

Therefore, the pre-processing signals 04 and spectral processing 06 may be subjected to further processing 08, carrying out:

The identification 10 of the presence of motor states similar to symptoms due to Parkinson's disease, Parkinsonism, and extrapyramidal symptoms;

The identification 12 of the temporal instances in which there are motor states similar to symptoms due to Parkinson's disease, Parkinsonism, and extrapyramidal symptoms;

The quantification 14 of the extent of the motor states that are similar to symptoms due to Parkinson's disease, and Parkinsonism, and extrapyramidal symptoms.

More specifically, processing 08 may include the execution of the identification 10 of the presence of motor states similar to symptoms due to Parkinson's disease, Parkinsonism, and extrapyramidal symptoms by combining the evaluation of a characteristic frequency content and the presence of patterns associated with peculiar movements. In fact, it is noted in the research that tremors in Parkinson's disease are typically characterized by a pronation-supination movement between 3 and 7 Hz, while tremors due to essential tremors are typically characterized by a flexion-extension movement between 3 and 12 Hz. Moreover, the phenomenology of individual patient dyskinesia typically tends not to change over time.

Figures 9, 9A, 9B:
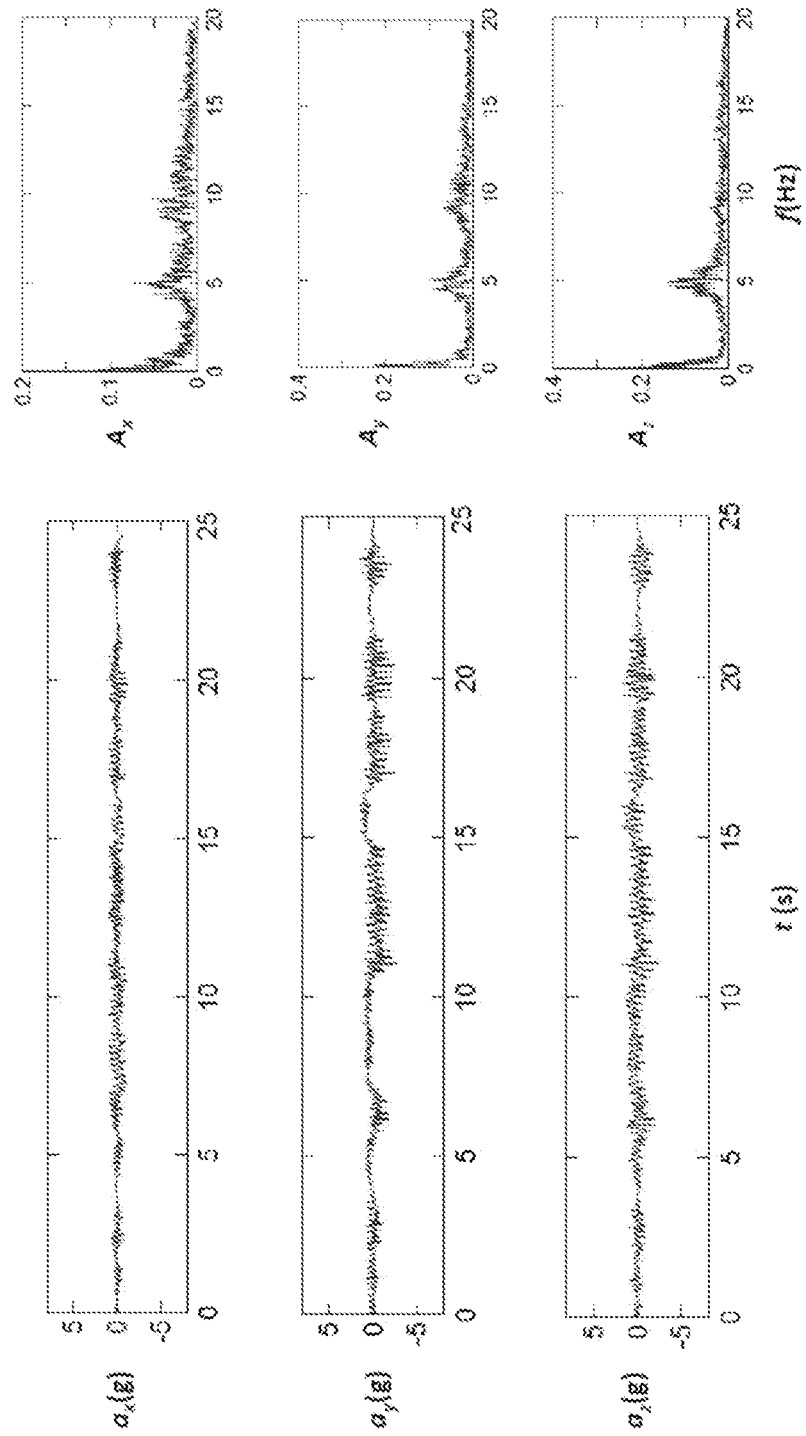
FIG. 9 schematically illustrates the temporal and frequency trends of the wrist monitoring device in the case of an essential tremor.

With reference to FIGS. 8 and 9, the trends are shown as a function of time t and of the trend in function of the frequency f respectively referring to a patient affected by Parkinsonian tremors and to a patient with tremors due to essential tremors.

By way of example, FIGS. 8A and 9A show for each of the three axes (x, y and z), the acceleration time trends ($a_x$, $a_y$ and $a_z$) detected by the triaxial accelerometric measuring system 22 which is worn on the wrist; these trends were obtained using a sampling frequency of 100 Hz for each axis and considering the pre-processing process 04, as described above.

By way of example, the trends in FIG. 8 show that, net of the low frequency contribution and due to frequencies lower than about 1 Hz, a frequency contribution is predominant in the range between 4 and 7 Hz, i.e. within the frequency range in which Parkinsonian tremors usually occur. FIG. 8B also shows that the frequency contribution between 3 and 7 Hz detected at the x-axis results in a greater contribution than the frequency contribution between 3 and 7 Hz detected at the y-axis and the frequency contribution between 3 and 7 Hz detected at the x-axis, results in a greater contribution than the frequency contribution between 3 and 7 Hz detected at the z-axis. Moreover, FIG. 8B also shows that the frequency contribution between 3 and 7 Hz detected at the z-axis results in a greater contribution than the frequency contribution between 3 and 7 Hz detected at the y-axis. FIG. 8A also shows that the maximum amplitude of the $a_x$ acceleration is greater than both the maximum amplitude of the acceleration $a_y$ and the maximum amplitude of the acceleration $a_z$. Finally, FIG. 8A also shows that the maximum amplitude of the acceleration $a_z$ is greater than the maximum amplitude of the acceleration $a_y$.

By way of example, the trends shown in FIG. 9 demonstrate that, net of the low frequency contribution and due to frequencies lower than about 1 Hz, a frequency contribution of approximately 5 Hz is predominant. Moreover, it also possible to observe non-negligible frequency content between 8 and 9 Hz. These contributions fall within the frequency range in which tremors due to essential tremors usually occur. In addition, FIG. 9B shows that the frequency content between 3 and 10 Hz detected at the z-axis results in a greater contribution than the frequency contribution between 3 and 10 Hz detected at the x-axis and that the frequency contribution between 3 and 10 Hz detected in correspondence with the y-axis is higher than the frequency contribution between 3 and 10 Hz detected at the x-axis. FIG. 9A also shows that the maximum amplitude of the acceleration $a_z$ is greater than the maximum amplitude of the $a_x$ acceleration. Finally, FIG. 8A also shows that the maximum $a_y$ acceleration amplitude is greater than the maximum amplitude of the $a_x$ acceleration.

Therefore, processing 08 and identification 10 may include identification and discrimination of a specific pattern of motion associated with an extrapyramidal symptom by using a multi-axial measurement system and by quantifying the way the frequency content is detected, in certain characteristic frequency ranges and in a given time interval, is distributed and allocated on the various axes of the multi-axial measurement system.

Thus, in a possible configuration of the present invention, the identification 10, 12 and the quantification 14 of motor states similar to the extrapyramidal symptom may be performed by evaluating the characteristic frequency content detected on the individual axes (single axis evaluation) and the comparative evaluation between the characteristic frequency contents detected on the individual axes (inter-axes evaluation). In another realization, processing 08 and identification 10 may include the simultaneous identification of more specific movement patterns. In another realization, processing 08 and identification 10 may include the simultaneous identification of more specific movement patterns associated with various extrapyramidal symptoms.

In one realization, processing 08 may include identification 10, 12 and quantification 14 of the extent of motor states similar to symptoms due to Parkinson's disease, Parkinsonism, and extrapyramidal symptoms, also in terms of severity and duration. In another realization, in addition to, or as an alternative to the previous ones, the quantification 14 of the extent of the symptoms experienced may be carried out by the computation of synthetic numerical values, scores, and/or indices. In another realization, in addition to, or as an alternative to the previous ones, the quantification of 14 of the extent of motor states similar to symptoms may be performed by combining the computation of synthetic numerical values, scores, and/or indices, and the qualitative evaluation of the quantitative time-frequency analysis. In one realization, the qualitative evaluation of the quantitative time-frequency analysis may be carried out by examining the spectral analyzes and/or the time-frequency analyzes, and/or the trend over time of the synthetic numerical values, scores, and/or indices detected. In one realization, the examination of the time-frequency analyzes and/or the trend over time of the synthetic numerical values, scores, and/or indices detected may be performed by examining the graphic and/or numerical representation of the time-frequency analyzes and the graphic representation of the trend over time of synthetic numerical values, scores, and/or indices detected.

In another realization, in addition to, or as an alternative to the previous one, signal processing 08 may include the use of a smoothing filter to process the sequence of synthetic numerical values, scores, and/or indices detected; in the preferred realization, the smoothing filter is a mobile average filter.

Figure 10:
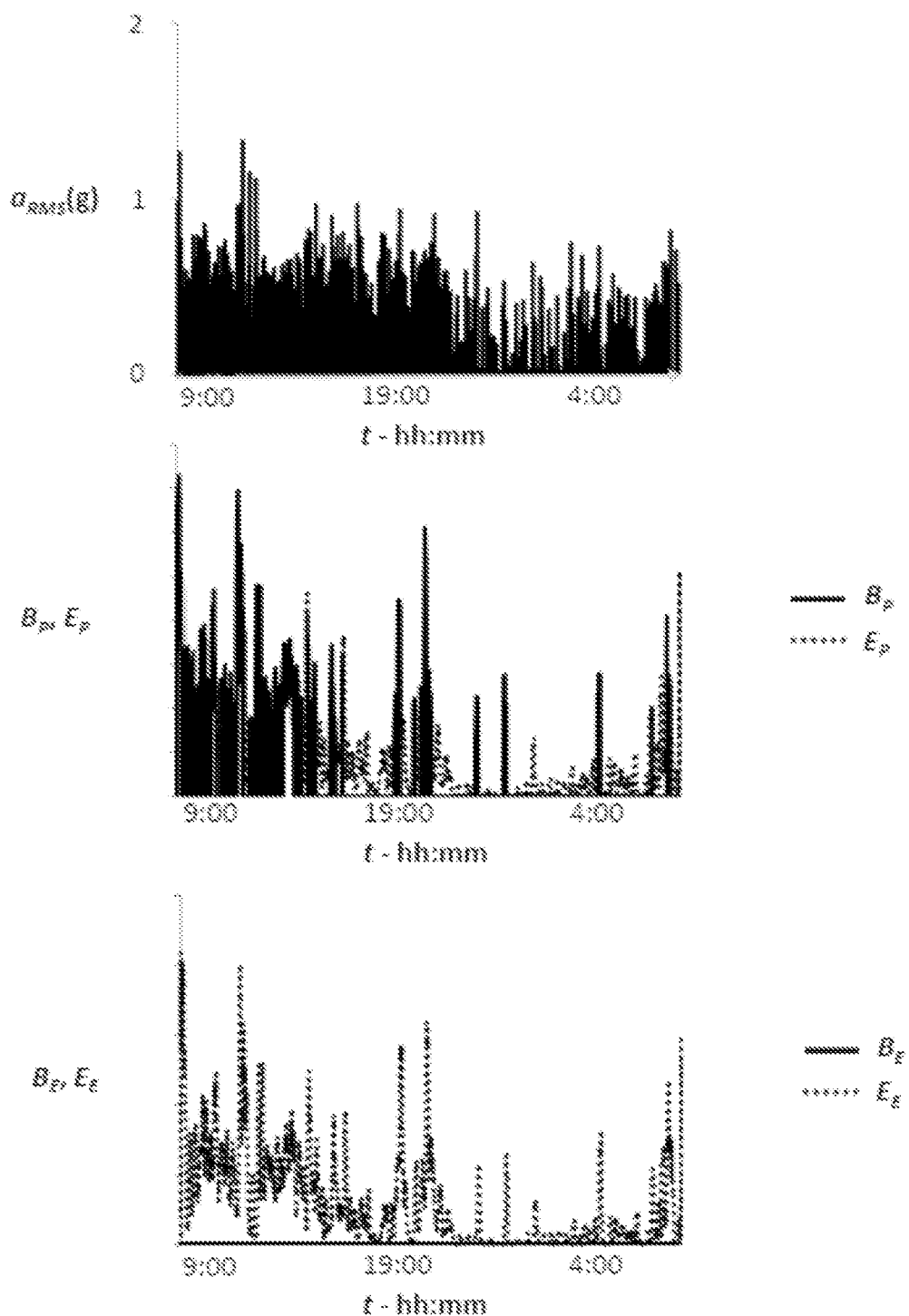
FIG. 10 schematically illustrates some of the possible results deriving from the data processing of the wrist monitor in the case of a Parkinsonian tremor.
Figure 11:
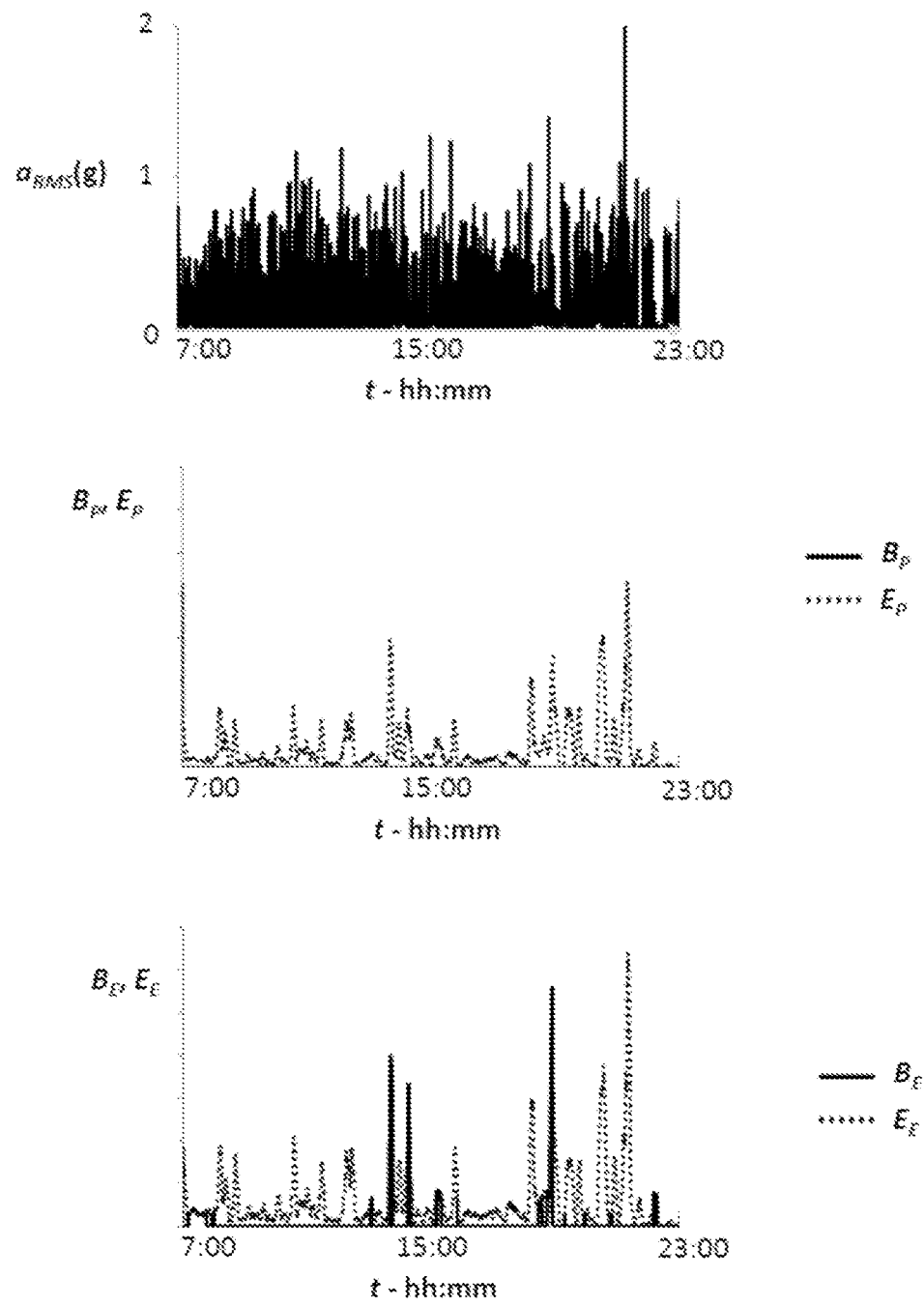
FIG. 11 schematically illustrates some of the possible results deriving from the data processing of the wrist monitoring device in the case of an essential tremor.
Figure 12:
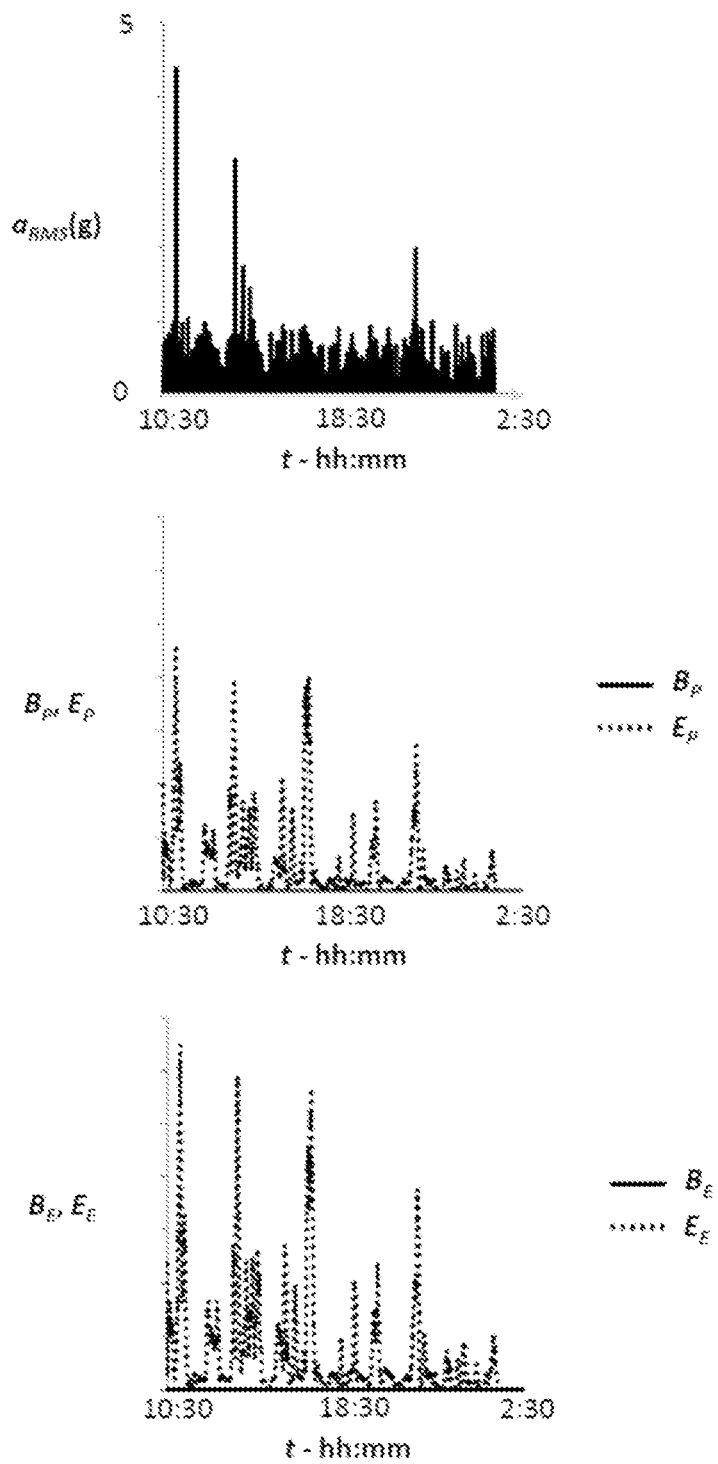
FIG. 12 schematically illustrates some of the possible results deriving from the data processing of the wrist monitoring device that does not seem to be affected by movement disorders.

FIGS. 10, 11, and 12 schematically illustrate some of the results that may be obtained from processing 08; FIG. 10 illustrates the processes that refer to a patient with tremors due to Parkinson's disease, FIG. 11 illustrates the processes that refer to a patient suffering from an essential tremor, and FIG. 12 illustrates the processes that refer to a "control" patient that appears not to be affected by neurological diseases that cause movement disorders.

In more detail, processing 08 may include the execution of the identification of the presence of motor states similar to Parkinsonian tremors through the combination of the evaluation of a characteristic frequency content, and the presence of movement patterns due to pronation-supination. This characteristic frequency content may be evaluated over a frequency range that may include values between 3 and 7 Hz. In one realization, in addition to, or as an alternative to the previous ones, the combination of the evaluation of a characteristic frequency content and of the presence of movement patterns due to pronation-supination may include the evaluation of the characteristic frequency content detected on the single axes (single axis evaluation) and the comparative evaluation between the characteristic frequency contents detected on the individual axes (inter-axes evaluation). In one realization, in addition to, or as an alternative to the previous ones, with respect to identification 10, this presence of movement patterns due to pronation-supination may be identified at the time intervals for which all of the following three conditions occur:

$$\begin{cases} E_{Px} > E_{Pz} + \sigma_{xz} \\ E_{Px} > E_{Py} + \sigma_{xy} \\ E_{Pz} > E_{Py} + \sigma_{zy} \end{cases} \quad (5)$$

this possible pattern of movement is namely identified at each sub-interval for which we have:

$$(Q_P) \text{ AND } (W_P) \text{ AND } (R_P) = 1 \quad (6)$$

where $\sigma_{xz}$, $\sigma_{xy}$, and $\sigma_{zy}$ are threshold values, AND binary logical operator, AND the parameters $Q_P$, $W_P$, $R_P$ are defined as:

$$Q_P = \begin{cases} 1, & se \ E_{Px} > E_{Pz} + \sigma_{xz} \\ 0, & se \ E_{Px} \le E_{Pz} + \sigma_{xz} \end{cases}$$

$$W_P = \begin{cases} 1, & se \ E_{Px} > E_{Py} + \sigma_{xy} \\ 0, & se \ E_{Px} \le E_{Py} + \sigma_{xy} \end{cases}$$

$$R_P = \begin{cases} 1, & se \ E_{Pz} > E_{Py} + \sigma_{zy} \\ 0, & se \ E_{Pz} \le E_{Py} + \sigma_{zy} \end{cases}$$

Essentially, if the conditions of the previous formula (6) are met, this is indicative of a pronation-supination movement that is characteristic of a condition for a Parkinson's disease tremor. This analysis, therefore, allows for the distinction between a voluntary movement from a movement that is due to this specific pathology.

In one realization, the aforesaid threshold values are defined as follow: $\sigma_{zy}=0$, $\sigma_{xz}=\sigma_{xy}=\sigma$, where $\sigma$ is a constant value for all the sub-intervals. In one realization, in addition to, or as an alternative to the previous ones, processing 08 may include identification of the pronation-supination movement associated with a Parkinsonian tremor, considering all the time intervals for which the following occurs:

$$(Q_P^{rel}) \text{ AND } (W_P^{rel}) \text{ AND } (R_P^{rel}) = 1 \quad (7)$$

where $\sigma_{xz}^{rel}$, $\sigma_{xy}^{rel}$ and $\sigma_{zy}^{rel}$ are threshold values, AND is the binary logical operator, AND the parameters $Q_P^{rel}$, $W_P^{rel}$, $R_P^{rel}$ are defined as:

$$Q_P^{rel} = \begin{cases} 1, & se \ E_{Px}^{rel} > E_{Pz}^{rel} + \sigma_{xz}^{rel} \\ 0, & se \ E_{Px}^{rel} \le E_{Pz}^{rel} + \sigma_{xz}^{rel} \end{cases}$$

$$W_P^{rel} = \begin{cases} 1, & se \ E_{Px}^{rel} > E_{Py}^{rel} + \sigma_{xy}^{rel} \\ 0, & se \ E_{Px}^{rel} \le E_{Py}^{rel} + \sigma_{xy}^{rel} \end{cases}$$

$$R_P^{rel} = \begin{cases} 1, & se \ E_{Pz}^{rel} > E_{Py}^{rel} + \sigma_{zy}^{rel} \\ 0, & se \ E_{Pz}^{rel} \le E_{Py}^{rel} + \sigma_{zy}^{rel} \end{cases}$$

In one, such threshold values are defined as follows: $\sigma_{zy}^{rel}=0$, $\sigma_{xz}^{rel}=\sigma_{xy}^{rel}=\sigma^{rel}$, where $\sigma^{rel}$ is a constant value for all the sub-intervals.

In another realization, the value of the a threshold or the value of the threshold $\sigma^{rel}$ may be selected by considering a statistical value identified by previous observations, or a percentage value of reference, or the energy contribution due to a reference signal r(t); by way of example, the reference signal may be:

$$r(t) = 14 \cdot \text{sinc}(14 \cdot t) - 6 \cdot \text{sinc}(6 \cdot t) \quad (8)$$

In one realization, as better illustrated below, for the same patient, such threshold values $\sigma$ and/or $\sigma^{rel}$ may be considered as a reference for comparing the motor state between multiple continuous monitoring sequences that have been carried out over time.

In one realization, processing 08 may include identification 12 of the temporal instants in which a Parkinsonism like tremor motor state has occurred, by detecting the time instances associated with the sub-intervals of the monitoring sequence in which the identification of a tremor motor state has been identified according to one of the previous realizations, or when the condition of equation (6) occurs, or when the condition of equation (7) occurs.

In one realization, processing 08 may include quantification 14 of the extent of the motor state similar to a Parkinson's disease tremor. In one realization, the quantification 14 of the extent of a motor state similar to tremors from Parkinson's disease may be carried out in terms of severity and/or duration. In one realization, the quantification 14 of the extent of the motor state similar to Parkinson's disease. In one realization, the quantification 14 of the extent of a motor state similar to a Parkinson's disease tremor may include the evaluation of the overall frequency content detected at a frequency range that may include the values included in the intervals between 3 and 7 Hz.

In one realization, the quantification 14 of the extent of the motor state similar to a Parkinson's disease tremor may be performed by the computation of synthetic numerical values, scores, and/or indices. In another realization, in addition to, or as an alternative to the previous ones, the quantification 14 of the extent of the motor state similar to a Parkinson's disease tremor may be performed combining the computation of synthetic numerical values, scores, and/or indices, and qualitative evaluation of quantitative time-frequency analysis.

In one realization, the quantification 14 of the extent of a motor state similar to a Parkinson's disease tremor may be calculated in terms of duration through the computation of one or more indices, including the $L_P$ index. In one realization, in addition to, or as an alternative to the previous one, the quantification 14 of the extent of the motor state similar to a Parkinsonian tremor may be calculated in terms of the severity by the computation of one or more indices, including the $B_P$ index, and/or the $B_P^{TOT}$ index, and/or the $\overline{B_P}$ index. In one realization, in addition to, or as an alternative to the previous one, the quantification 14 of the extent of the motor state similar to a Parkinsonian tremor may be calculated in terms of the severity by the computation of one or more indices, including the $BL_P^{TOT}$ index and the $\overline{BL_P^{TOT}}$ index. In one realization, in addition to, or as an alternative to the previous one, the quantification 14 of the extent of the motor state similar to a Parkinsonian tremor may be calculated in terms of the severity by the computation of one or more indices, including the $BL_P$ index, obtained by multiplying the $BL_P^{TOT}$ index and/or $\overline{BL_P^{TOT}}$ index by a coefficient.

In one realization, in addition to, or as alternative to the previous one, the quantification of the extent of the motor state of a Parkinsonism type tremor in terms of duration may be obtained by evaluating the total $N_P$ number of time sub-intervals of the monitoring sequence in which the presence of this motor state similar to previously mentioned symptoms is identified in accordance with that indicated in the previous realizations. In one realization, in addition to, or as an alternative to the previous one, the quantification of the extent of the motor state of a Parkinsonism type tremor in terms of duration may also be obtained possibly with the computation of an $L_P$ index, by evaluating the total duration number of time sub-intervals of the monitoring sequence in which the presence of the motor state similar to that symptom has been identified in accordance with that indicated in the previous realizations. In the preferred realization, the $L_P$ index may be calculated by means of the product between $N_P$ and the duration of each sub-interval $\Delta t$. In another realization, the quantification of the extent of the motor state similar to a Parkinsonian tremor in terms of duration may include, possibly also with the computation of an $L_P$ index, the percentage assessment of the relationship between the cumulative duration of the tremor detected during the monitoring period and the total duration of the monitoring sequence. In another realization, the quantification of the extent of the motor state similar to a Parkinsonian tremor in terms of duration may include, possibly also with the computation of an $L_P$ index, the percentage ratio between the cumulative duration of a tremor detected during the monitoring period and the cumulative $T_{AR}$ time in which a motor activity is detected (or the value of $E_P$) above a certain threshold during the monitoring period.

In one realization, processing 08 may include the quantification 14 of the extent of the motor state similar to a Parkinsonian tremor in terms of severity, possibly also by the computation of a $B_P$ index, obtained by considering the sub-intervals in which the identification 10 was carried out of the possible presence of a motor state similar to a Parkinsonian tremor and the frequency content, evaluated in the characteristic frequency range of the tremor, detected on all the axes of the measurement system. In one realization, the $B_P$ index may take zero value at the time sub-intervals for which the possible presence of Parkinsonian tremors has not been identified, and may take the value equal to $E_{P,RMS}$ in correspondence with the time sub-intervals for which the possible presence of a Parkinsonian tremor was identified according to the previous realizations. In another realization, the $B_P$ index may take zero value at the time sub-intervals for which the possible presence of Parkinsonian tremors have not yet been identified, and may take the value equal to $E_P$, as defined in equation (2) or the combination of equations (2) and (3), corresponding to the time sub-intervals for which the possible presence of Parkinsonian tremor have been identified according to previous realizations. In another realization, the contribution provided by each axis to the $B_P$ value may be calculated (by way of example, it is possible to calculate $B_{Px}=E_{Px}$, $B_{Py}=E_{Py}$, $B_P=E_{Pz}$). In another realization, in addition to, or as an alternative to the previous ones, the $B_P$ index may be a dimensionless and normalized parameter with respect to the reference unit value $E_{P,REF}$. By way of example, but not limitation, two possible computations of the $B_P$ parameter are reported:

$$B_P = \frac{E_P}{E_{P,REF}} \quad (9a)$$

$$B_P = \frac{E_{P,RMS}}{E_{P,REF}} \quad (9b)$$

In one realization, the parameter $E_{P,REF}$ may be evaluated considering the reference signal (8). In another realization, the $B_P$ index may be obtained by a linear or non-linear combination of the $E_{Px}$, $E_{Py}$ and $E_{Pz}$ parameters. In one realization, in addition to, or as an alternative to the previous ones, the $B_P$ index may be computed as follows:

$$B_P = \frac{E_{Px} \cdot E_{Pz}}{E_{Py}} \quad (10)$$

In another realization, in addition to, or as an alternative to the previous ones, the quantification of the severity of the tremor may include the computation of the above parameters $E_{P,RMS}$, $E_{Px}$, $E_{Py}$, $E_{Pz}$, $E_{P,REF}$ through the use of a logarithmic function, the square root, or other mathematical functions.

By means of example, FIGS. 10, 11, and 12 refer to three different monitoring systems, respectively, of a patient with Parkinson's disease and with Parkinsonian tremors, of a patient suffering from essential tremors and tremors, and a "control" patient. FIGS. 10A, 11A, and 12A show the trend over time of the mean quadratic value of the $a_{RMS}$ acceleration, while FIGS. 10B, 11B, and 12B show in a continuous line the trend over time of the $B_P$ index, evaluated according to the equation (9a), and in a dotted line the trend over time of the value $E_P$, where $E_P$ is evaluated according to equations (2) and (3) (or according to another of the previously reported realizations). Therefore, the $B_P$ index assumes the zero value in the case in which the motor activity is not detected due to the motor state similar to a Parkinsonian tremor, while it assumes the same value of the $E_P$ parameter, for those sub-intervals in correspondence with those that reveal the possible presence of a motor state similar to a Parkinsonian tremor. FIGS. 11B and 12B, related respectively to a patient with essentials and to a "control" patient, therefore show that there is no motor activity similar to a Parkinsonian tremor. FIG. 10B, which relates to a patient with a Parkinsonian tremor, shows that motor activity similar to a Parkinsonian tremor is present, confirming that not all the motor activities that determine non-zero content frequencies between 3 and 7 Hz are related to extrapyramidal symptoms and Parkinsonian tremors. FIGS. 10, 11, and 12 also show that it is possible to discriminate a Parkinsonian tremor from a tremor due an essential tremor.

In another realization, the processing 08 may include:

The computation of the $B_P$ index for all the time sub-intervals of the sequence according to what is reported in the formula (2), namely in the formulas (2) and (3), that is in one of the formulas (8), (9), and (10).

The identification 10, 12 of the motor state similar to a Parkinsonian tremor, evaluating the sub-intervals for which the $B_P$ index value is higher than a threshold value.

The quantification 14 of the motor state similar to a Parkinsonian tremor by evaluating the $B_P$ value only for those sub-intervals in which the previously mentioned identification 10 was carried out.

Therefore, from the previously mentioned realizations, it is possible to define a $B_P$ index for each single sub-interval of the entire monitoring sequence. However, it is possible to define an overall index to summarize the level of severity for the entire duration of the monitoring, alongside the $L_P$ index that may refer to the total duration of the tremor during the entire monitoring period.

In one realization, the quantification 14 of the motor state similar to a Parkinsonian tremor in terms of severity may include the overall evaluation of the indices related to the various sub-intervals. In one realization, the quantification 14 of the motor state similar to a Parkinsonian tremor in terms of severity may include the index calculation:

$$B_P^{TOT} = \Sigma B_P \qquad (11)$$

obtained by summing the value of all the $B_P$ indexes relative to all the sub-intervals of the monitoring sequence. In another realization, the quantification 14 of the motor state similar to a Parkinsonian tremor in terms of severity may include the calculation of the index, which, in the preferred realization, represents the mean value of all the $B_P$ values. In another version, the quantification 14 of the motor state similar to a Parkinsonian tremor in terms of severity may include the calculation of the $\overline{B_P}$ index, which, in the best realization, represents the mean value of all the $B_P$ values. In another realization, the $\overline{B_P}$ index may be calculated as a function of the ratio between $B_P^{TOT}$ and the number of sub-intervals in which the possible presence of a motor state similar to a Parkinsonian tremor has been identified. In another realization, the $\overline{B_P}$ index represents the mean value of all non-zero $B_P$ values.

In one realization, the quantification 14 of the motor state similar to a Parkinson's disease tremor both in terms of severity and duration may include the calculation of the $BL_P^{TOT}$ index and the $\overline{BL_P}^{TOT}$ index:

$$BL_P^{TOT} = L_P \cdot B_P^{TOT}, \overline{BL_P}^{TOT} = L_P \cdot \overline{B_P} \qquad (12)$$

In another realization, in addition to, or as an alternative to the previous ones, the quantification 14 of the motor state similar to a Parkinson's disease tremor in terms of intensity and/or duration may include the computation of all the indices mentioned above.

In another realization, in addition to, or as an alternative to the previous ones, the quantification 14 of the motor state similar to a Parkinson's disease tremor in terms of intensity and/or duration may include the graphic representation of the numerical parameters and indices detected during the entire monitoring sequence. In an illustrative realization, the sequence of the values of the indices detected at each interval (e.g. $B_P$, $E_{P,RMS}$, $E_{Px}$, $E_{Py}$, $E_{Pz}$) may be reordered, in ascending or descending order, and displayed in a graph, as shown schematically, in FIG. 13A, in which it is also possible to graphically identify the $L_P$ index (equal to the $N_P * \Delta t$ product) representative of the cumulative time of the Parkinsonian tremor over the duration of monitoring, identified in correspondence with the time value, detected on the abscissa axis, for which the first non-zero $B_P$ index value is obtained. In another illustrated realization, the sequence of the values of the indices detected at each interval (e.g. $B_P$, $E_{P,RMS}$, $E_{Px}$, $E_{Py}$, $E_{Pz}$) may be reordered, in ascending or descending order to represent the cumulative distribution function, as illustrated schematically in FIG. 13C, in which it is possible to identify graphically:

The $L_P$ index (equal to the $N_P * \Delta t$ product), representative of the cumulative time of the motor state similar to a Parkinsonian tremor over the duration of the monitoring, identified in correspondence with the time value, measured on the abscissa axis, for which the first value of the cumulative function is other than zero;

The $B_P^{TOT}$ index, identified at an extreme high value, measured on the axis of the ordinates, of the cumulative function.

Figure 13:
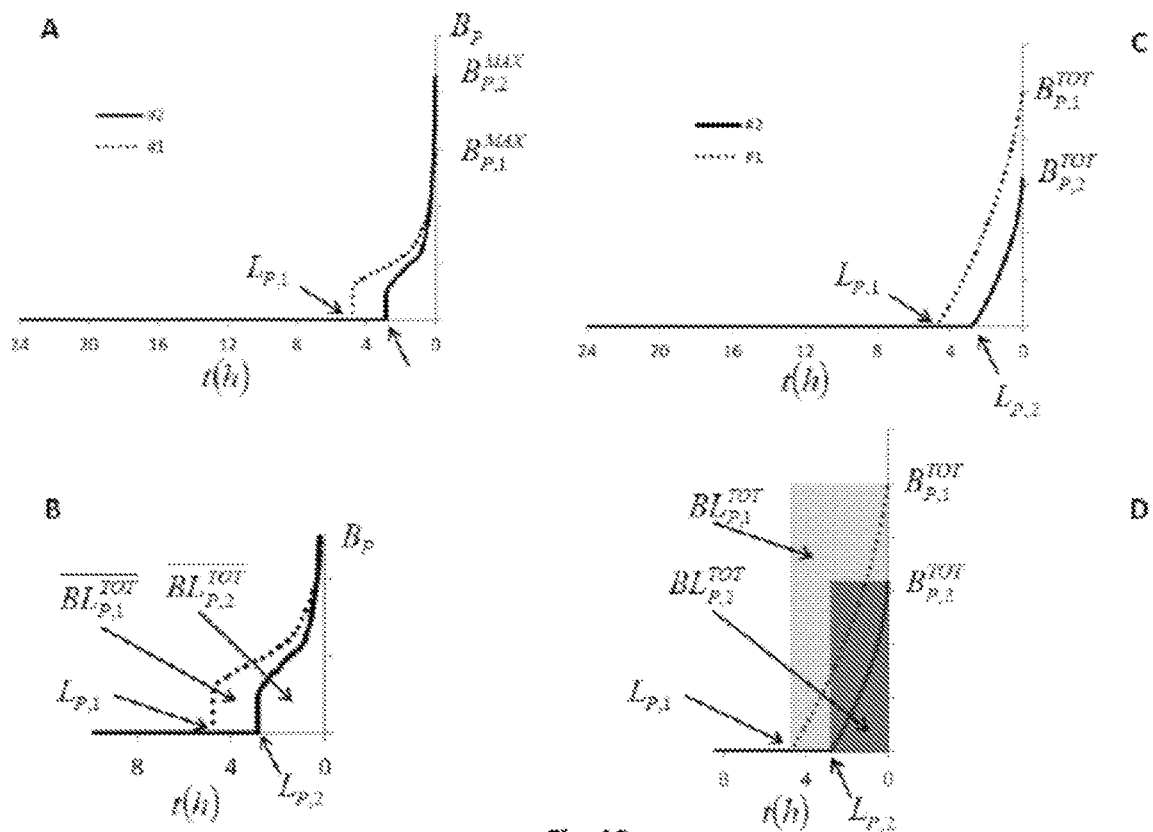
FIG. 13 schematically illustrates the graphic display of the indices detected during two different monitoring sequences of a patient with a Parkinsonian tremor.

In one realization, the graphic display of the indices detected during the monitoring sequence may be used to compare multiple monitoring sequences performed over time. FIG. 13 shows the graphic displays mentioned above for two different monitors performed on the same patient.

In another realization, in addition to, or as an alternative to the previous ones, the quantification 14 of the extent of the motor state similar to a Parkinson's disease may include:

The computation of synthetic numerical values, scores, and/or indices (including the $B_P$, $B_{Dx}$, $B_{Dy}$, $B_{Dz}$, $E_{P,RMS}$, $E_{Px}$, $E_{Py}$, $E_{Pz}$ indices) and their trends related to the duration of the monitoring, as schematically illustrated in FIGS. 10, 11, and 12;

The computation of synthetic numerical values, scores, and/or indices (including the $L_P$, $N_P$, $BL_P$, $T_{AR}$, $B_P^{TOT}$, $\overline{BL_P}^{TOT}$, $BL_P^{TOT}$ and $\overline{B_P}$ indices) relative to the entire duration of the monitoring;

The graphic representation of these indices, including the mode illustrated schematically in FIG. 13.

The qualitative evaluation of quantitative time-frequency analysis.

In one realization, in addition to, or as an alternative to the previous ones, the qualitative evaluation of the quantitative time-frequency analysis may be carried out by examining the spectral analyzes and/or the time-frequency analyzes. This examination of spectral analyzes and/or time-frequency analyzes may be performed by examining the graphic and/or numerical representation of time-frequency analyzes and may include the examination of:

The trend over time of the parameters and the accelerations on the individual axes, as schematically shown in FIGS. 4A and 5A;

The overall frequency content of the entire monitoring sequence on the individual axes, as schematically shown in FIGS. 4B and 5B;

The spectrogram and/or the power density of the individual axes as a function of time and frequency, as schematically illustrated in FIGS. 6 and 7, and/or the spectrogram of the mean square value as a function of time and frequency.

In the preferred embodiment, the examination of the spectrograms and/or the power densities as a function of time and frequency may be aimed at facilitating the execution of a synthetic analysis of the results of the monitoring sequence through the visual consultation of the graphs, from which it is possible to have an indication of:

The way the frequency content is distributed over the entire monitoring sequence;

The frequency of occurrence of motor activity events in the frequency content of interest;

The presence of motor activity in intervals of frequencies adjacent to those used for the calculation of the indices and in other frequency ranges;

The intensity of motor activity events in the frequency content of interest;

The number of motor activity events in the frequency content of interest.

By way of example, by visually consulting the graphs shown in FIG. 6, the presence, especially in the initial part of the monitoring, of motor activity in the interval of interest between 3 and 7 Hz may be seen, namely in the interval in which the Parkinsonian tremor is typically verified. Other events are instead visible, with a lower frequency of occurrence, in the rest of the monitoring sequence. Moreover, a motor activity is observed, approximately half way through the monitoring sequence, in which harmonics appear, whose content, starting from the frequency of 10 Hz, decreases and appears to drop considerably after 20 Hz.

Figures 14A, 14B:
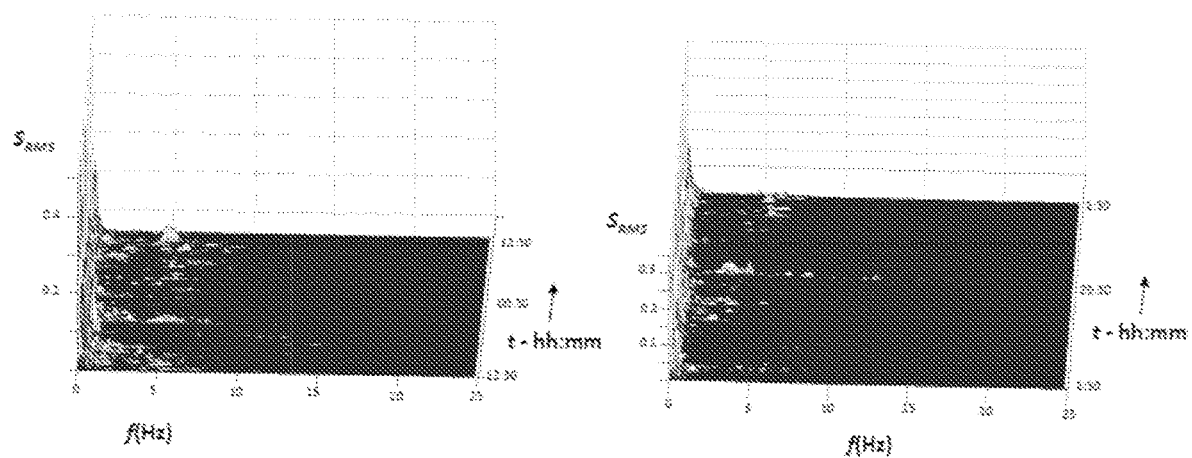
FIG. 14A illustrates the first monitoring.
FIG. 14B illustrates the second monitoring.

In another realization, in addition to, or as an alternative to the previous ones, the quantification 14 of the extent of the motor state similar to a Parkinson's disease tremor may include all the steps and elements previously indicated not only for the quantification of a single monitoring sequence, but also for quantification 14 and comparative evaluation 16 of multiple monitoring sequences. In fact, such a realization may be used to compare multiple monitoring sequences against each other and multiple monitoring sequences of the same patient to check the progress of his or her motor state over time, and possibly, the variation in his or her motor state as a function of variations to his or her therapeutic plan. By way of an illustrative example, FIG. 13 shows the graphic display of the indices detected during two different monitoring sequences related to the same patient. The second sequence refers to an acquisition in which the therapeutic plan followed by the patient turns out to be different from the first, as the dosage of the dopaminergic drug has been increased. Similarly, by way of illustrative example, FIG. 14 shows the graphic display of the power density for two different monitoring sequences relating to the same patient; the second sequence refers to an acquisition in which the therapeutic plan followed by the patient turns out to be different from the first, as the dosage of the dopaminergic drug has been increased. FIGS. 13A and 13B (enlargement of FIG. 13A around the origin of the Cartesian axes) show, for each sequence, the trend of the indices, in increasing order. FIG. 13B shows, for each sequence, the trend of the indices in terms of cumulative distribution functions. FIG. 13 shows that, although the maximum value of the $B_P$ index has been reached in the second acquisition sequence ($B_{P,2}^{MAX} < B_{P,1}^{MAX}$), from an overall point of view, the cumulative duration of the tremor and the value of the $L_P$ index of the second sequence are lower than that of the first ($L_{P,1} < L_{P,2}$). Moreover, the value of the $B_P^{TOT}$ index of the second monitoring sequence is lower than the value of the same index relative to the first monitoring sequence ($B_{P,2}^{TOT} < B_{P,1}^{TOT}$). Similarly, the index value of the second monitoring sequence $\overline{B_P}$ is lower than the value of the same index relative to the first monitoring sequence ($\overline{B_{P,2}} < \overline{B_{P,1}}$). Moreover, by way of example, it is possible to verify from FIG. 13A that the area under the curves present in the graph is different, where that underlying area is a function of the $B_P^{TOT}$ index value. Therefore, the difference between the areas under the curves in FIG. 13 and the difference of the values of the indices $B_P^{TOT}$ related to different monitoring sequences, may be used to compare different monitoring sequences and to support the evaluation of the variations in the monitoring sequences and to support the evaluation of the variations of the monitoring of the motor state of the patient between monitoring sequences. Similarly, the values of $\overline{BL_P^{TOT}}$, which, in one realization, correspond to the areas under each curve as shown schematically in FIG. 13A and FIG. 13B (enlargement of FIG. 13C around the origin of the Cartesian axes) and the values of $BL_P^{TOT}$, considering, in one realization, the area as shown schematically in FIGS. 13C and 13D (enlargement of FIG. 13C around the origin of the Cartesian axes). Finally, in another realization, the comparative evaluation 16 may be carried out by evaluating the areas under which the different cumulative distribution functions are associated, each individual $BL_P$ index associated with a monitoring system (in this way, the value of the $BL_P$ index may correspond with the value of the area under the curve). In another realization, the comparative evaluation 16 may be carried out by evaluating the histograms of the index values of each monitoring sequence. In another realization, schematically illustrated in FIG. 14, the comparative evaluation 16 may be carried out by evaluating, for each monitoring sequence, the spectrograms of the average quadratic value of the acceleration. In fact, by way of example, the graphs schematically illustrated in FIG. 14 show that the motor activity in the intervals of frequency between 3 and 7 Hz relative to the second monitoring sequence appears decidedly lower than that of the first monitoring sequence.

In one realization, processing 08 may include performing the identification of the presence of the motor state similar to a tremor due to essential tremors through the combination of the evaluation of a characteristic frequency content and the presence of motion pattern due to flexion-extension. In one realization, in addition to, or as an alternative to the previous ones, this characteristic frequency content may be evaluated over a frequency range that may include the frequency values ranging from 3 to 12 Hz. In one realization, in addition to, or as an alternative the previous ones, the combination of the evaluation of a characteristic frequency content and the presence of movement patterns due to flexion-extension may include the evaluation of the characteristic frequency content detected on the individual axes (single axis evaluation) and the comparative evaluation between the characteristic frequency contents detected on the individual axes (inter-axes evaluation). In one realization, in addition to, or as an alternative to the previous ones, with reference to identification 10, this presence of movement patterns due to flexion-extension may be identified at the time intervals for which all the following two conditions occur:

$$\begin{cases} E_{Ez} > E_{Ex} + \delta_{zx} \\ E_{Ey} > E_{Ex} + \delta_{yx} \end{cases} \quad (13)$$

This possible pattern of movement is namely identified at each sub-interval for which there is:

$$(Q_E) \text{ AND } (W_E)=1 \quad (14)$$

where $\delta_{zx}$ and $\delta_{yx}$ are threshold values, AND is the binary logical operator, AND the parameters $Q_E$ and $W_E$ are defined as:

$$Q_E = \begin{cases} 1, & se \ E_{Ez} > E_{Ex} + \delta_{zx} \\ 0, & se \ E_{Ez} \le E_{Ex} + \delta_{zx} \end{cases}$$

$$W_E = \begin{cases} 1, & se \ E_{Ey} > E_{Ex} + \delta_{yx} \\ 0, & se \ E_{Ey} \le E_{Ex} + \delta_{yx} \end{cases}$$

In one realization, the previously mentioned threshold values are defined as follows: $\delta_{zx}=\delta_{yx}=\delta$, where $\delta$ is a constant value for all sub-intervals.

In one realization, the presence of these movement patterns due to flexion-extension may be identified at the time intervals for which the following conditions occur:

$$(Q_E) \text{ OR } (W_E)=1$$

where OR is the binary logical operator OR.

In one realization, the presence of movement patterns due to flexion-extension may be identified at the time intervals for which the following conditions occur:

$$E_{Ez} > E_{Ex} + \delta_{zx}$$

In one realization, in addition to, or as an alternative to the previous ones, processing 08 may include identification of the flexion-extension associated with tremor due to essential tremors, considering all the time intervals for which the following occurs:

$$(Q_E^{rel}) \text{ AND } (W_E^{rel})=1 \quad (15)$$

where $\delta_{zx}^{rel}$ and $\delta_{yx}^{rel}$ are threshold values, AND is the binary logical operator AND the parameters $Q_E^{rel}$ are $W_E^{rel}$ defined as:

$$Q_E^{rel} = \begin{cases} 1, & se \ E_{Ez}^{rel} > E_{Ex}^{rel} + \delta_{zx}^{rel} \\ 0, & se \ E_{Ez}^{rel} \le E_{Ex}^{rel} + \delta_{zx}^{rel} \end{cases}$$

$$W_E^{rel} = \begin{cases} 1, & se \ E_{Ey}^{rel} > E_{Ex}^{rel} + \delta_{yx}^{rel} \\ 0, & se \ E_{Ey}^{rel} \le E_{Ex}^{rel} + \delta_{yx}^{rel} \end{cases}$$

In one realization, such threshold values are defined as follows: $\delta_{zx}^{rel}=\delta_{yx}^{rel}=\delta^{rel}$, where $\delta^{rel}$ is a constant value for all such sub-intervals.

In one realization, the value of the $\delta$ threshold or the value of the $\delta^{rel}$ threshold may be selected by considering a statistical value identified by previous observations or by considering a percentage value of reference, or by considering the energy contribution due to a reference signal. In one realization, as further detailed below, for the same patient, the threshold values $\delta$ and/or $\delta^{rel}$ may be considered as a reference when comparing the patient's motor state between multiple continuous monitoring sequences performed over time.

In one realization, processing 08 may include identification 12 of the temporal instances in which the motor state similar to a tremor occurred due to an essential tremor by detecting the temporal instances associated with the sub-intervals of the monitoring sequence in which the identification 10 of the motor state similar to a tremor according to one of the previous realizations is verified, or when the condition referred to in equation (14) occurs, or when the condition referred to in equation (15) occurs.

In one realization, processing 08 may include quantification 14 of the extent of the motor state similar to a tremor due to an essential tremor. In one realization, the quantification 14 of the magnitude of the motor state similar to a tremor due to an essential tremor may be performed in terms of severity and/or duration. In one realization, the quantification 14 of the extent of the motor state similar to an essential tremor may include the evaluation of the overall frequency content and the evaluation of the frequency content detected at a frequency range that may includes the values comprised in the range between 3 and 12 Hz.

In one realization, the quantification 14 of the magnitude of the motor state similar to a tremor due to an essential tremor may be achieved by the computation of synthetic numerical values, scores, and/or indices. In another realization, in addition to, or as an alternative to the previous ones, the quantification 14 of the extent of the motor state similar to a tremor due to an essential tremor may be performed by combining the computation of synthetic time-frequency analysis.

In one realization, the quantification 14 of the extent of the motor state similar to a tremor due to an essential tremor may be achieved in terms of the duration through the computation of one or more indices, including the $L_E$ index. In one realization, in addition to, or as an alternative to the previous ones, the quantification 14 of the extent of the motor state similar to a tremor due to an essential tremor may be achieved in terms of severity through the computation of one or more indices, including the $B_E$ index and/or $B_E^{TOT}$ index and/or $\overline{B_E}$ index. In one realization, in addition to, or as an alternative to the previous ones, the quantification 14 of the extent of the motor state similar to a tremor due to an essential tremor may be achieved in terms of both the severity and the duration through the computation of one or more indices, including the $BL_E^{TOT}$ index and the $\overline{BL_E}^{TOT}$ index. In one realization, in addition to, or as an alternative to the previous ones, the quantification 14 of the extent of the motor state similar to a tremor due to an essential tremor may be achieved in terms of both the severity and the duration through the computation of one or more indices, including the $BL_E$ index, obtained by multiplying the $BL_E^{TOT}$ index and/or the $\overline{BL_E}^{TOT}$ index by a coefficient.

In one realization, in addition to, or as an alternative to the previous ones, the quantification of the extent of tremors due to essential tremors in terms of duration may be obtained by evaluating the total number of time sub-intervals of the monitoring sequence in which the presence of this symptom, according to what has been indicated in the previous realizations, is identified. In one realization, in addition to, or as an alternative to the previous ones, the quantification of the extent of tremors due to essential tremors in terms of duration may also be eventually obtained through the computation of the $L_E$ index, by evaluating the total number of time sub-intervals of the monitoring sequence in which the presence of this symptom, according to what has been indicated in the previous realizations, is identified. In the preferred realization, the $L_E$ index may by calculated by computing the product between $N_E$ and the duration of each sub-interval $\Delta t$. In another realization, the quantification of the extent of tremors due to essential tremors in terms of duration may also eventually include the computation of the $L_E$ index, the evaluated percentage of the relationship between the cumulative duration of the tremor due to an essential tremor detected during the monitoring period and the total duration of the monitoring sequence. In another realization, the quantification of the extent of tremors due to essential tremors in terms of duration may include the evaluation, eventually also with the computation of the $L_E$ index, of the percentage ratio between the cumulative duration of the tremor due to an essential tremor detected during the monitoring sequence and the cumulative $T_{AR}$ time in which a motor activity is detected (or the value $E_E$) above a certain threshold during the monitoring period.

In one realization, the processing 08 may include quantification 14 of the extent of the tremor due to an essential tremor in terms of severity eventually also through the computation of the $B_E$ index, obtained by considering the time sub-intervals in which the identification 10 of the possible presence of the motor state similar to a tremor due to an essential tremor and the content frequency, evaluated in the characteristic frequency range of the tremor due to an essential tremor, detected on all the axes of the measurement system. In one realization, the $B_E$ index may take the zero value at the time sub-intervals for which the possible presence of the motor state similar to a tremor due to an essential tremor has not been identified, and may assume the value equal to $E_{E,RMS}$, in correspondence with the time sub-intervals for which the possible presence of a motor state similar to an essential tremor, according to the previous realizations, has been identified. In another realization, the $B_E$ index may take the zero value at the time sub-intervals for which the possible presence of the motor state similar to a tremor due to an essential tremor has not been identified, and may assume a value equal to $E_E$, as defined in equation (2) or the combination of equations (2) and (3), in correspondence with the time sub-intervals for which the possible presence of a motor state similar to an essential tremor, according to the previous realizations, has been identified. In another realization, it is possible to compute the contribution provided by each axis to the value $B_E$ (for example, it is possible to calculate $B_{Ex}=E_{Ex}$, $B_{Ey}=E_{Ey}$, $B_{Ez}=E_{Dz}$). In another realization, in addition to, or as alternative to the previous ones, the $B_E$ index may be a dimensionless and normalized parameter with respect to a reference unit value $E_{E,REF}$. By way of example, but not limitation, two possible calculations of the $B_E$ parameter are reported:

$$B_E = \frac{E_E}{E_{E,REF}} \quad (16a)$$

$$B_E = \frac{E_{E,RMS}}{E_{E,REF}} \quad (16b)$$

In one realization, the parameter $E_{E,REF}$ may be evaluated by considering the reference signal (8). In another realization, the $B_E$ index may be obtained by a linear or non-linear combination of the $E_{Ex}$, $E_{Ey}$, and $E_{Ez}$ parameters. In another realization, in addition to, or as an alternative to the previous ones, the $B_E$ index may be calculated as follows:

$$B_E = \frac{E_{Ez} \cdot E_{Ey}}{E_{Ex}} \quad (17)$$

As illustrated, FIGS. 10, 11, and 12 refer respectively, as indicated above, to three different monitoring sequences, of a patient with Parkinson's disease and with Parkinsonian tremors, a patient suffering from essential tremors, and a "control" patient. FIGS. 10A, 11A, and 12A demonstrate the trend over time of the mean quadratic value of the $a_{RMS}$ acceleration, while FIGS. 10C, 11C, and 12C show in a continuous line the trend over time of the $B_E$ index, evaluated according to the equation (16a), and in the dotted line of the trend over time of the $E_E$ value, evaluated according to equations (2) and (3) (or according to another of the previously reported realizations). Therefore, the $B_E$ index assumes the zero-value in the case that no motor activity is detected due to an essential tremor, while it assumes the same value of the $E_E$ parameter, for those sub-intervals in which a possible presence of a tremor due to an essential tremor is detected. FIGS. 12C and 10C relate respectively to a "control" patient and a patient with a Parkinsonian tremor, therefore demonstrating that there are no motor activities similar to an essential tremor. FIG. 11C, which relates to a patient suffering from an essential tremor, demonstrates that there is motor activity similar to a tremor due to an essential tremor, confirming that not all motor activities which determine a non-zero frequency content between 3 and 12 Hz are linked to extrapyramidal symptoms and to a tremor due to an essential tremor. FIGS. 10, 11, and 12 also demonstrate that it is possible to discriminate a Parkinsonian tremor from a tremor due to an essential tremor.

In another realization, in addition to, or as alternative to the previous ones, the quantification of the severity of the motor state similar to a tremor due to an essential tremor may include the computation of the above parameters and the $E_{E,RMS}$, $E_{Ex}$, $E_{Ey}$, $E_{Ez}$, $E_{E,REF}$ parameters by using a logarithmic function, the square root, or other mathematical functions.

In another realization, the process 08 may include:

The computation of the $B_E$ index for all the time sub-intervals sequences as reported in formula (2), namely in formulas (2) and (3), namely in one of the formulas (8), (16) and (17);

The identification 10, 12 of a tremor due to an essential tremor by evaluating the sub-intervals for which the value of the $B_E$ index is higher than a threshold value;

The quantification 14 of the motor state similar to a tremor due to an essential tremor by evaluating the value of $B_E$ only for those sub-intervals in which the previously mentioned identification 10 was carried out.

Therefore, from the realizations previously mentioned, it emerges that it possible to define a value of the $B_E$ index for each single time sub-interval of the entire monitoring sequence. However, it is possible to define an overall index to summarize the level of severity for the entire duration of the monitoring, alongside the $L_E$ index, which may be referred to as the total duration of the motor state similar to a tremor during the entire monitoring sequence.

In one realization, the quantification 14 of a tremor due to an essential tremor in terms of severity may include the overall evaluation of the indices relative to the sub-intervals. In one realization, the quantification 14 of the motor state similar to an essential tremor in terms of severity may include the index calculation:

$$B_E^{TOT} = \Sigma B_E \quad (18)$$

obtained by summing the value of all the $B_E$ indices related to the all the sub-intervals of the monitoring sequence. In another realization, the quantification 14 of a tremor due to an essential tremor in terms of severity may include the calculation of the $\overline{B_E}$ index, which, in the preferred realization, represents the mean value of all the $B_E$ values. In another realization, the $\overline{B_E}$ index may be calculated as a function of the ratio between $B_E^{TOT}$ and the number of sub-intervals in which the possible presence of a motor state similar to an essential tremor has been identified. In another realization, the index $\overline{B_E}$ that represents the mean value of all $B_E$ values other than zero.

In one realization, the quantification 14 of a tremor due to an essential tremor in terms of both severity and duration may include the calculation of the $BL_E^{TOT}$ index and the $\overline{BL_E^{TOT}}$ index:

$$BL_E^{TOT} = L_E \cdot B_E^{TOT}, \overline{BL_E^{TOT}} = L_E \cdot \overline{B_E^{TOT}} \quad (19)$$

In another realization, in addition to, or as an alternative to the previous ones, the quantification 14 of s tremor due to as an essential tremor in terms of intensity and/or duration may include the computation of the all the indices mentioned above.

In another realization, in addition to, or as an alternative to the previous ones, the quantification 14 of a tremor due to an essential tremor in terms of intensity and/or duration may include the graphic representation of the numerical parameters and indices detected during the entire monitoring sequence. In an illustrated realization, the sequence of the values of the indices measured at each interval (e.g. $B_E$, $E_{E,RMS}$, $E_{Ex}$, $E_{Ey}$, $E_{Ez}$) may be reordered, in ascending or descending order, and displayed in a graph, similar to that illustrated previously in FIG. 13A, in which it is possible to also graphically identify the $L_E$ index (equal to the product $N_E * \Delta t$) representative of the cumulative time of a tremor due to an essential tremor over the duration of the monitoring, identified in correspondence with the time value, detected on the abscissa axis, for which the first $B_E$ index value different from zero is obtained. In another illustrated realization, the sequence of values measured at each interval (e.g. $B_E$, $E_{E,RMS}$, $E_{Ex}$, $E_{Ey}$, $E_{Ez}$) may be reordered, in ascending or descending order, to represent the cumulative function of distribution, similar to what has been previously illustrated in FIG. 13C. From this graph, it is possible to graphically identify:

The $L_E$ index (equal to the product $N_E * \Delta t$), representative of the cumulative time of the tremor due to an essential tremor over the duration of the monitoring sequence, identified in correspondence with the time value, measured on the abscissas axis, for which there is the first value of the cumulative function other than zero;

The $B_E^{TOT}$ index identified at an extreme high value, measured on the axis of the ordinates, of the cumulative function.

In one realization, the graphic display of the indices detected during the monitoring sequence may be used to compare multiple monitoring sequences performed over time, similarly to what is previously represented in FIG. 13.

In another realization, in addition to, or as an alternative to the previous ones, the quantification 14 of a tremor due to as an essential tremor may include:

The computation of synthetic numerical values, scores, and/or indices (including the $B_E$, $B_{Ex}$, $B_{Ey}$, $B_{Ez}$, $E_{E,RMS}$, $E_{Ex}$, $E_{Ey}$, $E_{Ez}$ indices) and their trends related to duration of monitoring, as schematically illustrated in FIGS. 10, 11, and 12;

The computation of synthetic numerical values, scores, and/or indices (including the $L_E$, $N_E$, $T_{AR}$, $LB_E$, $B_E^{TOT}$, $\overline{BL_E^{TOT}}$, $BL_E^{TOT}$ and $\overline{B_E}$ indices) relative to the entire monitoring period;

The graphic representation of these indices;

The qualitative evaluation of quantitative time-frequency analysis.

In one realization, in addition to, or as an alternative to the previous ones, the qualitative assessment of the quantitative time-frequency analysis may be carried out by examining the spectral analyzes and/or the time-frequency analyzes. This examination of the spectral analyzes and/or the time-frequency analyzes may be carried out by examining the graphic and/or numerical representations of time-frequency analyzes and may include the review of:

The trend over time of the parameters and accelerations on the individual axes;

The total frequency content of the entire monitoring sequence on the individual axes;

The spectrogram and/or the power density of the individual axes as a function of time and of the frequency and/or the spectrogram of the mean square value as a function of time and frequency.

In the preferred realization, the examination of the spectrograms and/or the power densities as a function of time and frequency may be aimed at facilitating the execution of a synthetic analysis of the monitoring results through the consultation of the graphs, from which it is possible to visually have an indication of:

The way the frequency content is distributed over the entire monitoring sequence;

The frequency in which motor activity events occur at in the frequency content of interest;

The presence of motor activity in intervals of frequency adjacent to those used for the calculation of the indices and other frequency ranges;

The intensity of motor activity events in the frequency content of interest;

The number of motor activity events in the frequency content of interest.

In another realization, in addition to, or as an alternative to the previous ones, the quantification 14 of a tremor due to as an essential tremor may include all the steps and elements previously indicated not only for the quantification 14 of a single monitoring sequence, but also for the quantification 14 and comparative evaluation 16 of multiple monitoring sequences. In fact, such a realization may be used to compare multiple monitoring sequences with each other and multiple monitoring sequences from the same patient to check the progress of his or her motor state over time, and possible variations to his or her motor state because of changes to his or her therapeutic plan. By way of an illustrated example, this display of the data may be carried out in a way that is similar to what has already been schematically illustrated in FIGS. 13 and 14.

Finally, in another realization, the comparative evaluation 16 may be performed by evaluating the areas under which the different cumulative distribution functions are each associated with a monitoring sequence. In another realization, comparative evaluation 16 may be performed by evaluating the histograms of the index values of each monitoring sequence. In another realization, comparative evaluation 16 may be performed by evaluating, for each monitoring sequence, the spectrograms of the average quadratic value of acceleration.

In one realization, the processing 08 may include identification 10, 12 and the quantification 14 of the extent of motor states similar to symptoms due to Parkinson's disease, Parkinsonism, and extrapyramidal symptoms, also in terms of severity and duration. In another realization, in addition to, or as an alternative to the previous ones, the quantification 14 of the extent of the symptoms experienced may be carried out through the computation of synthetic numerical values, scores, and/or indices. In another realization, in addition to, or as an alternative to the previous ones, the quantification 14 of the extent of the symptoms experienced may be carried out by combining the computation of synthetic numerical values, scores, and/or indices and the qualitative evaluation of the quantitative analysis time-frequency. In one realization, the qualitative evaluation of the quantitative time-frequency analysis may be carried out by examining the spectral analyzes and/or the time-frequency analyzes, and/or the trend over time of the synthetic numerical values, scores, and/or indices. In one realization, the examination of the time-frequency analyzes and/or the trend over time of the synthetic numerical values, scores, and/or indices detected may be carried out by examining the graphic and/or numerical representation of the time-frequency analyzes, and of the graphical representation of the trend over time of synthetic numerical values, scores, and/or indices detected.

In one realization, the process 08 may include the execution of the identification and quantification of motor states similar to dyskinesia by combining the evaluation of a characteristic frequency content and the presence of peculiar movement patterns. In one realization, in addition to, or as an alternative to the previous ones, this characteristic frequency content may be evaluated over a frequency range that may include the frequency values ranging from 1 to 3 Hz and from 3 to 8 Hz. In a realization, in addition to, or as an alternative to the previous ones, the combination of the evaluation of a characteristic frequency content and the presence of peculiar movement patterns may include the evaluation of the characteristic frequency content detected on a single axis (single axis evaluation) and the comparative evaluation among the characteristic frequency contents detected on the individual axes (inter-axes evaluation).

In another realization, the processing 08 may include:

The computation of the $B_D = E_D$ index for all the time sub-intervals of the sequence according to what is reported in the formula (2), namely in the formulas (2) and (3);

The identification 10, 12 of the possible dyskinesia, evaluating the sub-intervals for which the value of the $B_D$ index is higher than threshold value;

The quantification 14 of the possible dyskinesia, evaluating the $B_D$ value only for those sub-intervals in which the previously mentioned identification 10 was carried out.

In another realization, the process 08 may include quantification 14 of the dyskinesia entity. In one realization, the quantification of dyskinesia may be carried out in terms of severity and/or duration. In one realization, the quantification 14 of the extent of the motor state similar to dyskinesia may include the evaluation of the overall frequency content and the evaluation of the frequency content detected at a frequency range that may include the values in the interval between 1 and 8 Hz.

In one realization, the quantification 14 of the extent of the motor state similar to dyskinesia may be carried out through the computation of synthetic numerical values, scores, and/or indices. In another realization, in addition to, or as an alternative to the previous ones, the quantification 14 of the extent of the motor state similar to dyskinesia may be performed by combining the computation of synthetic numerical values, scores, and/or indices and the qualitative evaluation of the quantitative time-frequency analysis.

In one realization, the quantification 14 of the extent of the motor state similar to dyskinesia may be carried out in terms of duration through the computation of one or more indices, including the $L_D$ index. In one realization, in addition to, or as an alternative to the previous ones, the quantification 14 of the extent of the dyskinesia may be carried out in terms of the severity by computation of one or more indices, including the $B_D$ index and/or the $BL_D^{TOT}$ index and/or the $\overline{B_D}$ index. In one realization, in addition to, or as an alternative to the previous ones, the quantification 14 of the extent of the dyskinesia may be carried out both in terms of severity and duration through the computation of one or more indices, including the $BL_D^{TOT}$ index and the $\overline{BL_D^{TOT}}$ index. In one realization, in addition to, or as an alternative to the previous ones, the quantification 14 of the extent of the dyskinesia may be carried out both in terms of severity and duration through the computation of one or more indices, including the $BL_D$ index, obtained by multiplying the $BL_D^{TOT}$ index and/or the $\overline{BL_D^{TOT}}$ index by a coefficient.

In one realization, in addition to, or as an alternative to the previous ones, the quantification of the extent of the dyskinesia in terms of duration may be obtained by evaluating the total $N_D$ number of the time sub-intervals of the monitoring sequence in which the presence of dyskinesia, in accordance with what has been indicated in the previous realizations, has been identified. In one realization, in addition to, or as an alternative to the previous ones, the quantification of the extent of the dyskinesia in terms of duration may be obtained eventually also with the computation of an $L_D$ index, by evaluating the duration of the total number of time sub-intervals of the monitoring sequence in which the possible presence of dyskinesia, in accordance with what has been indicated in the previous realizations, has been identified. In the preferred realization, the $L_D$ index may be calculated through the product between $N_D$ and the duration of each sub-interval $\Delta t$. In another realization, the quantification of the extent of the dyskinesia in terms of duration may include, eventually also with the computation of an $L_D$ index, the percentage value of the relationship between the cumulative duration of the possible dyskinesia detected during the monitoring period, and the total duration of the monitoring. In another realization, the quantification of the extent of the dyskinesia in terms of duration may also include the eventual evaluation of an $L_D$ index, the percentage ratio between the cumulative $T_{AR}$ in which a motor activity is detected (or a value of $E_D$) above a certain threshold during the monitoring period.

In one realization, the processing 08 may include quantification 14 of the extent of the motor state similar to dyskinesia in terms of severity, eventually also by the computation of a $B_D$ index, obtained by considering the time sub-intervals in which the identification 10 of the possible presence of dyskinesia and the frequency content, evaluated in the frequency range characteristic of dyskinesia, detected on all the axes of the measurement system. In one realization, the $B_D$ index may take the zero value at the time sub-intervals for which the possible presence of dyskinesia has not been identified, and may assume the value equal to $E_{D,RMS}$ at the time intervals for which the possible presence of dyskinesia, in accordance with what has been indicated in the previous realizations, has been identified. In another realization, the $B_D$ index may take the zero value at the time sub-intervals for which the possible presence of dyskinesia has not been identified, and may assume the value equal to $E_D$, as defined in the equation (2) or the combination of equations (2) and (3), in correspondence with the time sub-intervals for which the possible presence of dyskinesia, in accordance with what has been indicated in the previous realizations, has been identified. In another realization, it is possible to compute the contribution provided by each axis of the value of $B_D$ (for example, it is possible to compute $B_{Dx}=E_{Dx}$, $B_{Dy}=E_{Dy}$, $B_{Dz}=E_{Dz}$). In another realization, in addition to, or as an alternative to the previous ones, the $B_D$ index may be a dimensionless and normalized parameter with respect to a reference unit value $E_{D,REF}$. By way of example, but not limitation, two possible computations of the $B_D$ parameter are reported:

$$B_D = \frac{E_D}{E_{D,REF}} \quad (20a)$$

$$B_D = \frac{E_{D,RMS}}{E_{D,REF}} \quad (20b)$$

In one realization, the parameter $E_{D,REF}$ may be evaluated by considering a reference signal. In another realization, the $B_D$ index may be obtained by a linear or non-linear combination of the $E_{Dx}$, $E_{Dy}$ and $E_{Dz}$ parameters.

In another realization, in addition to, or as an alternative to the previous ones, the quantification of the severity of the dyskinesia may include the computation of the above parameters as well as the $E_{D,RMS}$, $E_{Dx}$, $E_{Dy}$, $E_{Dz}$, $E_{D,REF}$ parameters through the use of a logarithmic function, the square root, or other mathematical functions.

In one realization, the quantification 14 of dyskinesia in terms of severity may include the overall evaluation of all the indices related to the various sub-intervals. In one realization, the quantification 14 of dyskinesia in terms of severity may include the index calculation:

$$B_D^{TOT} = \Sigma B_D \quad (21)$$

obtained by summing the value of all the $B_D$ indices related to all the sub-intervals of the monitoring sequence. In another realization, the quantification 14 of dyskinesia in terms of severity may include the calculation of the $\overline{B_D}$ index, which, in the most favorable realization, represent the mean value of all the $B_D$ values. In another realization, the $\overline{B_D}$ index may be calculated as a function of the ratio between $B_D^{TOT}$ and the number of sub-intervals in which the possible presence of dyskinesia has been identified. In another realization, the $\overline{B_D}$ index represents the mean value of all the non-zero $B_D$ values.

In another realization, the quantification 14 of dyskinesia both in terms of severity and duration may include the calculation of the $BL_D^{TOT}$ index and the $\overline{BL_D^{TOT}}$ index:

$$BL_D^{TOT} = L_D \cdot B_D^{TOT} \quad \overline{BL_D^{TOT}} = L_D \cdot \overline{B_D} \quad (22)$$

In another realization, in addition to, or as an alternative to the previous ones, the quantification 14 of dyskinesia in terms of intensity and/or duration may include the computation of all the previously mentioned indices.

In another realization, in addition to, or as an alternative to the previous ones, the quantification 14 of dyskinesia in terms of intensity and/or duration may include the graphic representation of the numerical parameters and indices detected during the entire monitoring period. In an illustrated realization, the sequences of the values of the indices detected at each interval (e.g. $B_E$, $E_{E,RMS}$, $E_{Ex}$, $E_{Ey}$, $E_{Ez}$) may be reordered, in ascending or descending order, and displayed in a graph, as shown schematically, in FIG. 16A, in which it is also possible to graphically identify the $L_D$ index (equal to the product $N_D*\Delta t$), representative of the cumulative time of the dyskinesia over the duration of the monitoring, identified in correspondence with the time value, measured on the abscissa axis, for which the first $B_D$ index value other than zero is obtained. In an illustrated realization, the sequences of the values of the indices detected at each interval (e.g. $B_D$, $E_{D,RMS}$, $E_{Dx}$, $E_{Dy}$, $E_{Dz}$) may be reordered, in ascending or descending order, and displayed in a graph, as shown schematically, in FIG. 16B. In FIG. 16B, it is possible to identify through the graph:

The $L_D$ index (equal to the product $N_D*\Delta t$), representative of the cumulative time of the dyskinesia over the entire duration of the monitoring period, identified in correspondence with the time value, measured on the abscissa axis, for which the first value of the cumulative function other than zero is obtained.

The $B_D^{TOT}$ index identified at the extreme high value, measured on the axis of the ordinates, of the cumulative function.

In one realization, the graphic display of the indices detected during the monitoring sequence may be used to compare multiple monitoring sequences performed over time (similar to what has been previously illustrated in FIG. 14).

Figure 15:
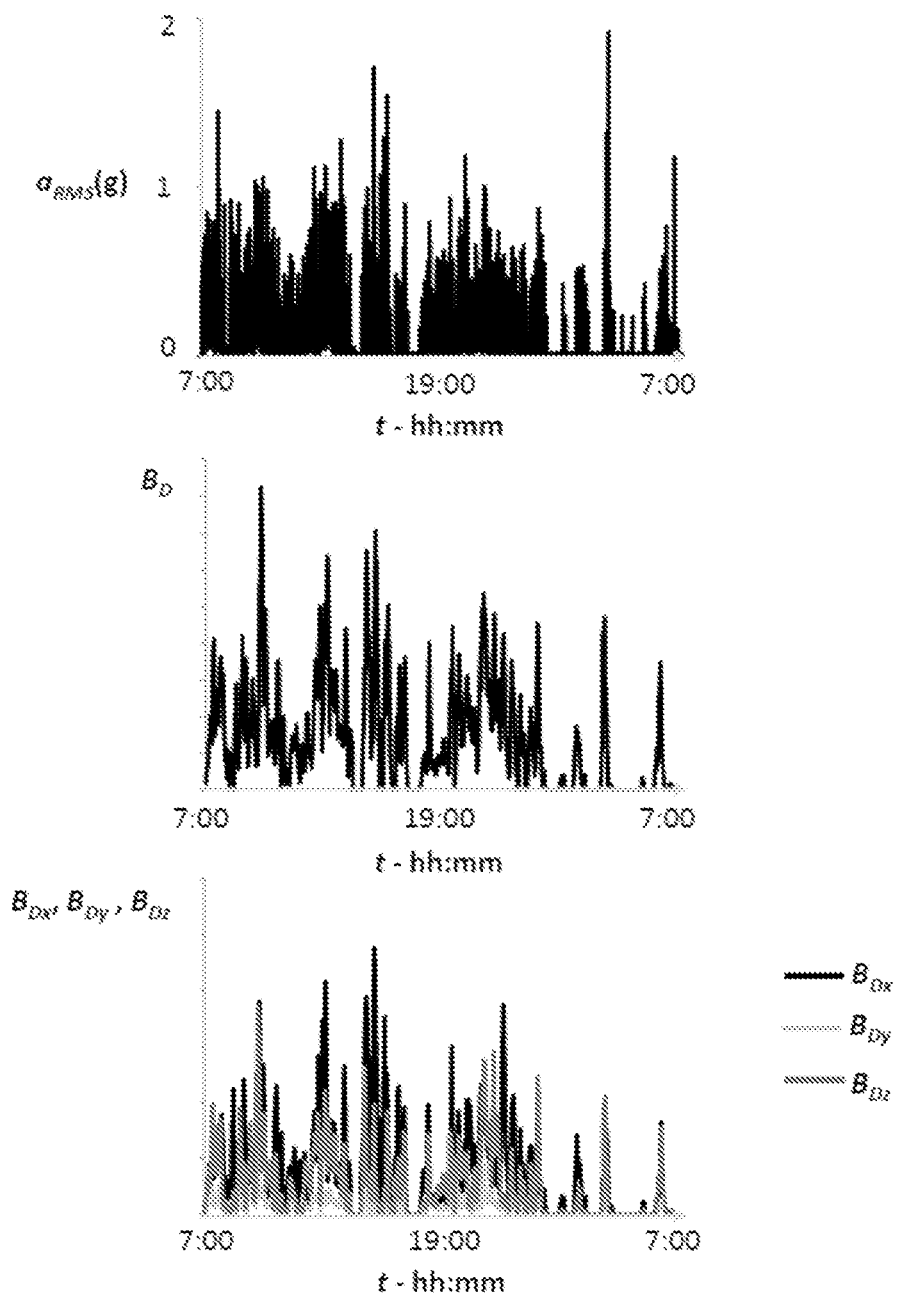
FIG. 15 schematically illustrates the trends of the indices to evaluate the dyskinesia, obtained by processing the traces shown in FIG. 5A and FIG. 7.
Figure 16:
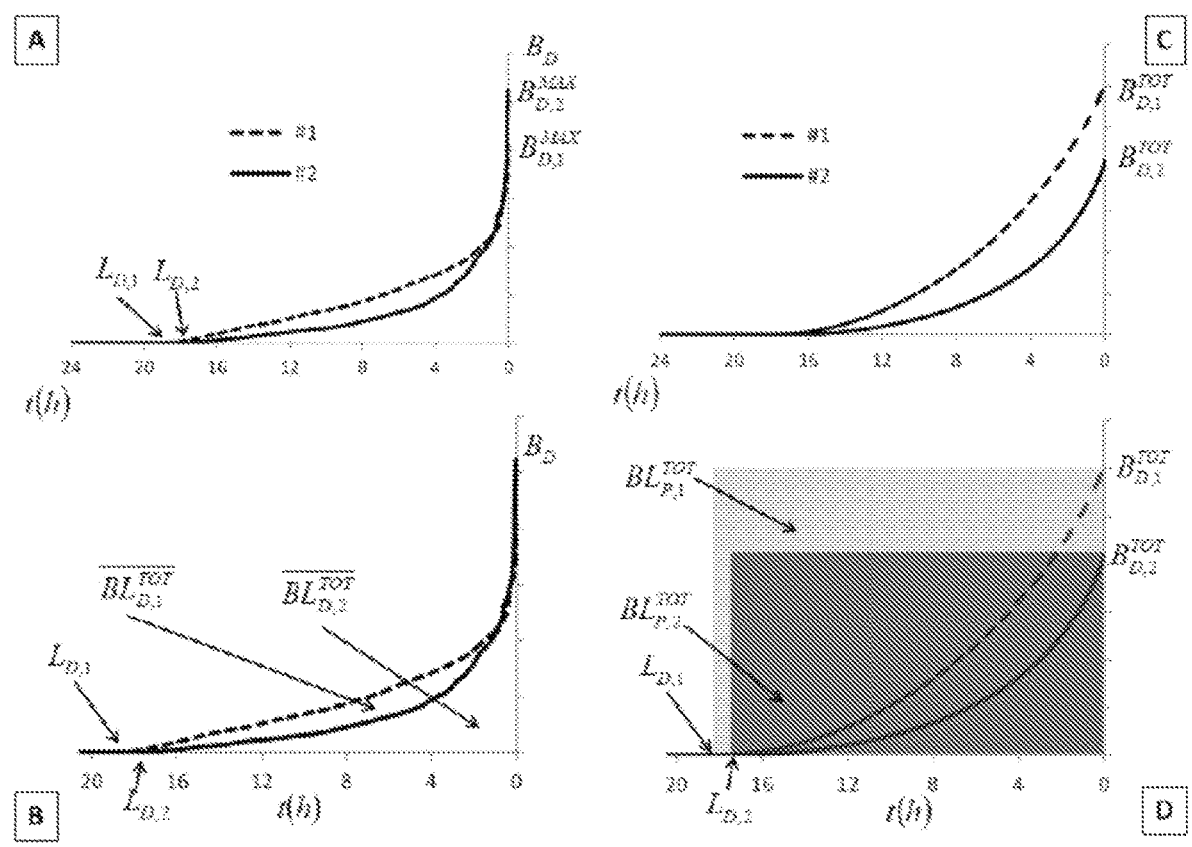
FIG. 16 schematically illustrates the graphic display of the indices detected during two different monitoring sequences of a patient with levodopa-induced dyskinesia.

In another realization, in addition to or as an alternative to the previous one, the identification 10, 12 and the quantification 14 of the extent of the motor state similar to dyskinesia may include:

The computation of synthetic numerical values, scores, and/or indices (including the $B_D$, $B_{Dx}$, $B_{Dy}$, $B_{Dz}$, $E_{D,RMS}$, $E_{Dx}$, $E_{Dy}$, $E_{Dz}$ indices) and their trend related to the monitoring duration, as schematically illustrated in FIG. 15;

The computation of synthetic numerical values, scores, and/or indices (including the $L_D$, $N_D$, $T_{AR}$, $BL_D$, $B_D^{TOT}$, $\overline{BL_D^{TOT}}$, $BL_D^{TOT}$ and $\overline{B_D}$ indices) relative to the entire duration of the monitoring period;

The graphic representation of these indices, including the mode schematically illustrated in FIG. 16.

The qualitative evaluation of quantitative time-frequency analysis.

In one realization, in addition to or as an alternative to the previous one, the qualitative evaluation of the quantitative time-frequency analysis may be carried out by examining the spectral analyzes and/or the time-frequency analyzes.

This examination of spectral analyzes and/or time-frequency analyzes may be performed by examining the graphic and/or numerical representation of time-frequency analyzes and may include the examination of:

The trend over time of the parameters and accelerations on the individual axes, as schematically shown in FIGS. 4A and 5A;

The overall frequency content of the entire monitoring sequence on the individual axes, as schematically shown in FIGS. 4B and 5B;

The spectrogram and/or the power density of the individual axes as a function of time and frequency, as schematically illustrated in FIGS. 6 and 7, and/or the spectrogram of the mean square value as a function of time and frequency.

In one realization, the examination of the spectrograms and/or the power densities as a function of time and frequency may be aimed at facilitating the execution of a synthetic analysis of the results of the monitoring through the consultation of the graphs, from which it is possible to have a visual indication of:

The way the frequency content is distributed over the entire monitoring sequence;

The frequency that motor activity events occur in the frequency content of interest;

The presence of motor activity in intervals of frequency adjacent to those used for the calculation of the indices and other frequency ranges;

The intensity of motor activity events in the frequency content of interest;

The number of motor activity events in the frequency content of interest.

In the preferred realization, the identification 10, 12 and the quantification 14 of dyskinesia is supported and carried out by the qualitative evaluation of the quantitative time-frequency analysis conducted through the examination of the spectrogram and/or the power densities as a function of time and frequency to evaluate the entire monitoring sequence, or part of it:

The extent of the frequency content in the interval that may include the frequency values ranging from 1 to 3 Hz and from 3 to 8 Hz, with respect to the entire spectral content;

The extent of the occurrence of motor activity events having prevalent frequency content in the range of 1 to 3 Hz and/or in the range of 3 to 8 Hz;

The extent of the spectral density value at motor activity events having prevalent frequency content in the range between 1 and 3 Hz and/or in the range between 3 and 8 Hz;

The extent of the difference between the value of the spectral density at the motor activity events with prevalent frequency content in the range between 1 and 3 Hz and/or 3 and 8 Hz, and the value of the spectral density at the remaining time sub-intervals of the acquisition sequence;

The way the frequency content (in correspondence with motor activity events with a prevalent frequency content in the range between 1 and 3 Hz and/or 3 and 8 Hz) is distributed over this interval.

This realization, in fact, takes into account the fact that the dyskinesia may occur, according to various modalities, mainly in the interval between 1 and 3 Hz, and, secondly, in the interval between 3 and 8 Hz, and that a patient affected by dyskinesia induced by Levodopa typically experiences a few moments of stillness, these movements usually being characterized a mean value of the spectral density greater than that of a healthy individual.

FIG. 7 schematically illustrates the occurrence of what is described above. In fact, the qualitative evaluation of the quantitative time-frequency analysis conducted through the examination of the spectrograms and/or the power densities as a function of time and frequency shows the following:

A predominant spectral contribution between 2.5 and 8 Hz, with specific reference to the interval between 3 and 5 Hz. Specifically, the negligible frequency content around 2 Hz is observed with respect to that of between 2.5 and 9 Hz;

The occurrence of such events between 2.5 and 9 Hz, for practically almost the entire duration of the monitoring;

These events are characterized by having a frequency content distributed over a wide range of frequencies, covering not only the interval between 3 and 5 Hz, but, in some cases, also up to 10 Hz;

The presence of certain sub-intervals in which the maximum value of the spectral density between 3 and 5 Hz is to the same extent as the maximum value evaluated for frequencies lower than 1 Hz.

Moreover, since the phenomenology of individual patient dyskinesia typically tends not to change over time, in another realization, as already indicated above, identification 10, 12 and quantification 14 of the extent of the motor state similar to dyskinesia may include the computation of the trend over time of synthetic numerical values, scores, and/or indices (including the $B_D$, $B_{Dx}$, $B_{Dy}$, $B_{Dz}$, $E_{D,RMS}$, $E_{Dx}$, $E_{Dy}$, $E_{Dz}$, indices). This indication may be used to evaluate the presence of characteristic movement patterns. By way of example, FIG. 15 shows the contribution provided by each axis ($B_{Dx}$, $B_{Dy}$, $B_{Dz}$) to the value $B_D$ evaluated on all the axes. This representation may be used to support the evaluation of peculiar movement patterns; for example, FIG. 15 shows, in addition to the $B_D$ trend, the contributions from the x-axis and the z-axis are also predominant with respect to the contribution on the y-axis.

In another realization, in addition to, or as an alternative to the previous ones, the quantification 14 of the extent of the dyskinesia may include all the steps and elements indicated above, not only for the quantification of a single monitoring, but also for the quantification 14 and the comparative evaluation 16 of multiple monitors. In fact, such a realization may be used to compare multiple monitoring sequences with each other and multiple monitoring sequences from the same patient to check the progress of his or her motor state over time, as well as possible variations to his or her motor state because of changes to his or her therapeutic plan. By means of an illustrated example, FIG. 16 shows the graphic display of the indices detected during two different monitoring sequences relating to the same patient. FIG. 16A shows, for each sequence, the trend of the indices, in ascending order. FIG. 16C shows, for each sequence, the trend of the indices in terms of cumulative distribution function. FIG. 16 shows that, although the maximum value of the $B_D$ index has been reach in the second acquisition sequence, from an overall point of view, the cumulative duration of the tremor, and the $L_D$ index value of the second sequence, are lower than the first ($L_{D,1} < L_{D,2}$). Moreover, the value of the $B_D^{TOT}$ index of the second monitoring sequence is lower than the value of the same index relative to the first monitoring sequence ($B_D^{TOT} < B_{D,1}^{TOT}$). Similarly, the index value of the second monitoring sequence $\overline{B_D}$ is lower than the value of the same index relative to the first monitoring sequence ($\overline{B_{D,2}} < \overline{B_{D,1}}$). Moreover, by way of example, it is possible to verify through FIG. 16A that the area under the curves present in the graph is different, where the underlying area is a function of the $B_D^{TOT}$ index value. Therefore, the difference between the areas under the curves in FIG. 16 and the difference in the values of the $B_D^{TOT}$ indices related to different monitoring sequences, may be used to compare different monitoring sequences and to support the evaluation of the patient's health between one monitoring session and another. Likewise, the values $\overline{BL_D^{TOT}}$ and $BL_D^{TOT}$ may also be evaluated through the graph by considering the areas as schematically shown in FIGS. 16C and 16D (enlargement of FIG. 16C around the origin of the Cartesian axes). Finally, in another realization, a comparative evaluation 16 may be carried out by evaluating the areas under the different cumulative distribution functions, each associated with a monitoring sequence, possibly identifying the $BL_D$ index for each monitoring sequence (in this case, the value of the $BL_D$ and/or $\overline{BL_D}^{TOT}$ indices may correspond or be proportional to the value of the underlying area). In another realization, a comparative evaluation 16 may be performed by evaluating the histograms of the index values in each monitoring session. In another realization, comparative evaluation 16 may be performed by evaluating, for each monitoring sequence, the spectrograms of the average quadratic value of acceleration.

In one realization, the processing 08 may include the execution of the identification and quantification of the motor state similar to bradykinesia by combining the evaluation of a characteristic frequency content and the presence of peculiar movement patterns. In one realization, in addition to, or as alternative to the previous ones, this characteristic frequency content may be evaluated over a frequency range that include frequency values from 02. To 3 Hz. In one realization, in addition to, or as alternative to the previous ones, the combination of the evaluation of a characteristic frequency content and the presence of peculiar movement patterns may include the evaluation of the characteristic frequency content detected on a single axis (single axis evaluation) and the comparative evaluation among the characteristic frequency contents detected on the individual axes (inter-axes evaluation).

In another realization, processing 08 may include:

The computation of the $B_B=1/E_B$ index for all the time sub-intervals of the sequence according to what is reported in the formula (2), namely in the formulas (2) and (3);

The identification 10, 12 of the motor state similar to a Parkinsonian tremor, evaluating the sub-intervals for which the $B_B$ index value is higher than a threshold value.

The quantification 14 of the possible dyskinesia, evaluating the $B_B$ value only for those sub-intervals in which the previously mentioned identification 10 was carried out.

In another realization, the $B_B$ index may be evaluated as $$B_B=a_{Bx}\cdot 1/E_{Bx}+a_{By}\cdot 1/E_{By}+a_{Bz}\cdot 1/E_{Bz}$$

In another realization, the process 08 may include quantification 14 of the extent of the motor state similar to bradykinesia; in one realization, the quantification 14 of the extent of bradykinesia may be carried out in terms of severity and/or duration. In one realization, the quantification 14 of the extent of the motor state similar to bradykinesia may include the evaluation of the overall frequency content and the evaluation of the frequency content detected as a frequency interval that may include values in the range of 0.2 and 3 Hz.

In one realization, the quantification 14 of the extent of the motor state similar to bradykinesia may be carried out by computing synthetic numerical values, scores, and/or indices. In another realization, in addition to, or as an alternative to the previous ones, the quantification 14 of the extent of the motor state similar to bradykinesia may be carried out by combining the computation of synthetic numerical values, scores, and/or indices, and the qualitative evaluation of the quantitative time-frequency analysis.

Similar to the previous realizations, the identification 10, 12 and the quantification 14 of the state of the motor state similar to bradykinesia may include:

The computation of synthetic numerical values, scores, and/or indices (including the $B_B$, $B_{Bx}$, $B_{By}$, $B_{Bz}$, $E_{B,RMS}$, $E_{Bx}$, $E_{By}$, $E_{Bz}$, indices) and their trend relative to the monitoring duration;

The computation of synthetic numerical values, scores, and/or indices (including the $L_B$, $N_B$, $T_{AR}$, $BL_B^{TOT}$, $\overline{BL_B}^{TOT}$, $BL_B^{TOT}$ and $\overline{B_B}$ indices) relating to the entire monitoring period;

The graphic representations of these indices;

Qualitative evaluation of quantitative time-frequency analysis.

In one realization, in addition to, or as alternative to the previous ones, the qualitative evaluation of the quantitative time-frequency analysis may be carried out by examining the spectral analyzes and/or the time-frequency analyzes.

This examination of spectral analyzes and/or time-frequency analyzes may be performed by examining the graphic and/or numerical representation of time-frequency analyzes and may include the examination of:

The trend over time of the parameters and accelerations of the individual axes;

The spectrogram total frequency content of the entire monitoring sequence on the individual axes;

The spectrogram and/or the power density of the individual axes as a function of time and of the frequency and/or the spectrogram of the mean square value as a function of time and frequency.

In one realization, the examination of the spectrograms and/or of the power densities as a function of time and frequency may be aimed at facilitating the execution of the synthetic analysis of the monitoring results through the visual consultation of the graphs, from which it is possible to have a visual indication of:

The way the frequency content is distributed over the entire monitoring sequence;

The frequency that motor activity events occur in the frequency content of interest;

The presence of motor activity in intervals of frequency adjacent to those used for the calculation of the indices and other frequency ranges;

The intensity of motor activity events in the frequency content of interest;

The number of motor activity events in the frequency content of interest.

Figure 17:
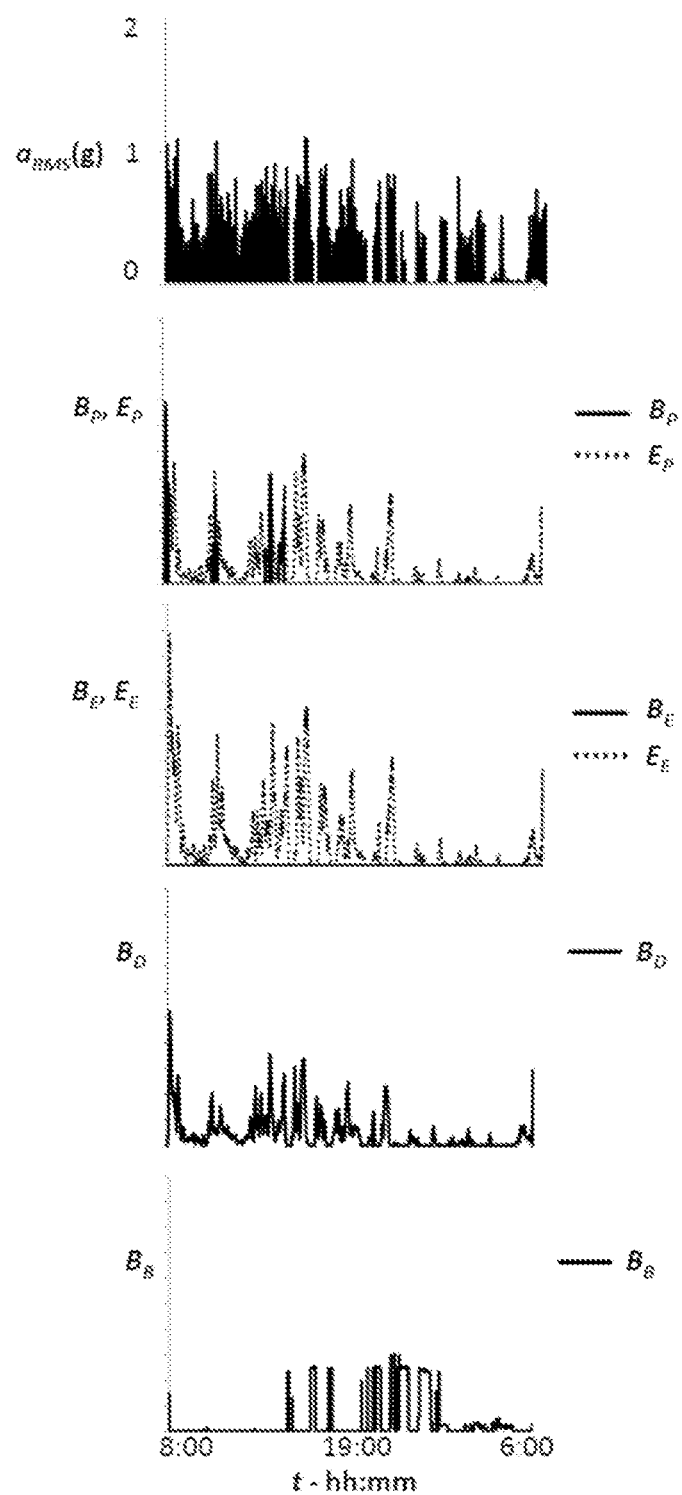
FIG. 17 schematically illustrates the graphic display of the Parkinsonian tremor indices, essential tremors, dyskinesia, and bradykinesia for monitoring sequences performed on patients affected by movement disorders.

As previously indicated and schematically shown in FIG. 17, in another realization, the processing 08 may include identification 10, 12 and quantification 14 of the extent of multiple motor states similar to multiple symptoms due to Parkinson's disease, Parkinsonism, and extrapyramidal symptoms on the same monitoring sequence.

Furthermore, in another realization, the processing 08 may include identification 10, 12 and quantification 14 of the extent of multiple motor states similar to multiple symptoms due to Parkinson's disease, Parkinsonism, and extrapyramidal symptoms on the same monitoring sequence, and the comparative evaluation 16 of the extent of multiple motor states similar to multiple symptoms due to Parkinson's disease, Parkinsonism, and extrapyramidal symptoms on the same monitoring sequence.

The present invention, although preferably directed towards the determination of movement disorders due to neurodegenerative diseases, may obviously be used to determine any motor state of a subject, even for non-diagnostic or medical purposes.

The invention claimed is:

1. A wearable device configured to determine a motor state of a subject comprising:
   a multi-axial measuring system adapted to detect at least one signal indicative of a motion of a limb or a plurality of parts of a body of the subject; and
   a processor programmed to perform;
      a spectral processing of the at least one signal by subdividing a monitoring sequence, during which the at least one signal is collected, into time sub-intervals and computing a Fourier transform at each axis of the multi-axial measurement system, wherein the spectral processing determines a frequency content of a signal at each axis of the multi-axial measurement system, and
      a comparison of the frequency content determined on each axis against a reference pattern to perform an inter-axes comparison between the frequency content determined on each axis and the reference pattern, to verify whether the frequency content determined on each axis matches the reference pattern to a predetermined degree.

2. The device, according to claim 1, wherein the spectral processing further comprises quantifying a distribution of the determined frequency content on each axis of the multi-axial measurement system by evaluating the frequency content determined on each axis of the multi-axial measurement system in predetermined characteristic frequency ranges and in predetermined time intervals, and comparing a determined characteristic frequency content determined on an individual axis of the multi-axial measurement system with a characteristic frequency content detected on another individual axis.

3. The device according to claim 2, wherein the processor is further programmed to carry out an identification of a motor state associated with Parkinson's disease tremor by determining whether the frequency content of each axis has a majority of frequencies included in intervals between 3 and 7 Hz, and further has frequencies generated by movement patterns due to pronation-supination.

4. The device according to claim 3, wherein determining whether the frequency content of each axis has frequencies generated by movement patterns due to pronation-supination comprises:
   computing a spectral density ($S_x$, $S_y$ and $S_z$) for each single axis of the multi-axial measurement system and in each time sub-interval of the monitoring sequence;
   computing, for the time sub-intervals and for each single axis, $E_{Px}$, $E_{Py}$ and $E_{Pz}$ parameters by integrating the respective spectral densities $S_x$, $S_y$ and $S_z$ over a characteristic frequency range between 3 Hz and 7 Hz; and
   identifying movement patterns due to the pronation-supination in correspondence with time sub-intervals for which all of the following three conditions occur:

$$\begin{cases} E_{Px} > E_{Pz} + \sigma_{xz} \\ E_{Px} > E_{Py} + \sigma_{xy} \\ E_{Pz} > E_{Py} + \sigma_{zy} \end{cases}$$

where $\sigma_{xz}$, $\sigma_{xy}$ and $\sigma_{zy}$ are threshold values.

5. The device according to claim 4, wherein a quantification of an extent of the motor state associated with Parkinson's disease tremor is provided by computing one or more numerical indices, comprising:

a $L_P$ index, whose computation includes evaluating a total number of time sub-intervals of the monitoring sequence in which a presence of the motor state associated with Parkinson's disease tremor is identified;
a $B_P$ index, having a zero value at time sub-intervals when pronation-supination patterns have not been identified, and, at other time sub-intervals, a value equal to $E_P$, defined as a linear or non-linear combination of the $E_{Px}$, $E_{Py}$ and $E_{Pz}$ parameters;
a $B_P^{TOT}$ index, obtained by adding values of all $B_P$ indices relative to all the sub-intervals of the monitoring sequence;
a $\overline{B_P}$ index, whose computation includes an evaluation of average value of all the $B_P$ values;
a $BL_P^{TOT} = L_P \cdot B_P^{TOT}$ index and a $\overline{BL_P^{TOT}} = L_P \cdot \overline{B_P}$ index;
a $BL_P$ index, obtained by multiplying the $BL_P^{TOT}$ and/or the $\overline{BL_P^{TOT}}$ indices by a coefficient;
$B_{Px} = E_{Px}$, $B_{Py} = E_{Py}$ and $B_{Pz} = E_{Pz}$ indices, representative of a contribution provided by each axis to the $B_P$ value evaluated on all the axes; and
additional indices obtained based on the $L_P$ index and/or the $B_P$ index.

6. The device, according to claim 1, wherein the processor is programmed to determine the frequency content of each axis in pre-determined time intervals.

7. The device according to claim 1, wherein the processor is programmed to carry out an identification of a motor state due to an essential tremor by determining whether the frequency content of each axis has a majority of frequencies included in an interval between 3 and 12 Hz and whether movement patterns due to flexion-extension are present.

8. The device according to claim 7, wherein determining whether movement patterns due to flexion-extension are present includes:
   subdividing the monitoring sequence into the time sub-intervals and computing a spectral density ($S_x$, $S_y$ and $S_z$) for each single axis of the multi-axial measurement system and in each time sub-interval of the monitoring sequence;
   computing, in individual time intervals and for each axis, $E_{Ex}$, $E_{Ey}$ and $E_{Ez}$ parameters by integrating the respective spectral densities $S_x$, $S_y$ and $S_z$ over a characteristic frequency range; and
   identifying movement patterns due to the flexion-extension at the time sub-intervals for which all of the following two conditions occur:

$$\begin{cases} E_{Ez} > E_{Ex} + \delta_{zx} \\ E_{Ey} > E_{Ex} + \delta_{yx} \end{cases}$$

where $\delta_{zx}$ and $\delta_{yx}$ are threshold values.

9. The device according to claim 8, in which the step of determining whether movement patterns due to the flexion-extension are present is carried out at the time sub-intervals for which the following condition occurs:

$$E_{Ez} > E_{Ex} + \delta_{zx}$$

10. The device according to claim 8, wherein a qualification of an extent of the motor state due to essential tremors is provided by a computation of one or more numerical indices, comprising:
   a $L_E$ index, whose computation includes calculating a total number of the time sub-intervals of the monitoring sequence in which the motor state has been identified;

a $B_E$ index, having a value of zero at time sub-intervals when flexion-extension patterns have not been identified, and having, at the other time sub-intervals, a value equal to $E_E$, defined as a linear or non-linear combination of the $E_{Ex}$, $E_{Ey}$ and $E_{Ez}$ parameters;

a $B_E^{TOT}$ index, obtained by adding a value of all the $B_E$ indexes related to all of the time sub-intervals of the monitoring sequence;

a $\overline{B_E}$ index, whose computation includes evaluating an average value of all of the $B_E$ values;

a $BL_E^{TOT}=L_E \cdot B_E^{TOT}$ index and a $\overline{BL_E^{TOT}}=L_E \cdot \overline{B_E}$ index;

a $BL_E$ index, obtained by multiplying the $BL_E^{TOT}$ index and/or the $\overline{BL_E^{TOT}}$ index by a coefficient;

$B_{Ex}=E_{Ex}$, $B_{Ey}=E_{Ey}$, e $B_{Ez}=E_{Ez}$ indices, representative of a contribution provided by each axis to the $B_E$ value evaluated on all of the axes; and additional indices obtained based on the $L_E$ index and/or the $B_E$ index.

11. The device according to claim 1, wherein the processor is programmed to perform an identification, quantification, and comparative evaluation of a motor state associated with dyskinesia by determining whether the frequency content of each axis has a majority of frequencies comprised in an interval between 1 and 8 Hz, and by performing the following steps:

subdividing the monitoring sequence into the time sub-intervals and computing the spectral density ($S_x$, $S_y$ and $S_z$) for each single axis of the multi-axial measurement system and in each time sub-interval of the monitoring sequence;

performing a computation, for the time sub-intervals and for each axis, of $E_{Dx}$, $E_{Dy}$ and $E_{Dz}$ parameters, by integrating the respective spectral densities $S_x$, $S_y$ and $S_z$ over a characteristic frequency range;

computing a $B_D$ index, where $B_D$ is defined as a linear or non-linear combination of the $E_{Dx}$, $E_{Dy}$ and $E_{Dz}$ parameters, for all of the time sub-intervals, identifying a possible dyskinesia by evaluating the time sub-intervals for which the $B_D$ index value is higher than a threshold value;

quantifying the possible dyskinesia by evaluating a value of the $B_D$ index only when the possible dyskinesia is identified;

computing one or more numerical indices, including:

a $L_D$ index, a computation of which includes calculating a total number of time sub-intervals of the monitoring sequence in which a presence of the possible dyskinesia was identified;

a $B_D^{TOT}$ index, obtained by adding values of all of the $B_D$ indices relative to all the time sub-intervals of the monitoring sequence;

a $\overline{B_D}$ index, a computation of which includes evaluating an average value of all of the $B_D$ values;

a $BL_D^{TOT}=L_D \cdot B_D^{TOT}$ index and a $\overline{BL_D^{TOT}}=L_D \cdot \overline{B_D}$ index;

a $BL_D$ index, obtained by multiplying the $BL_D^{TOT}$ index and/or the $\overline{BL_D^{TOT}}$ index by a coefficient;

$B_{Dx}=E_{Dx}$, $B_{Dy}=E_{Dy}$ and $B_{Dz}=E_{Dz}$ indexes, representative of a contribution provided by each axis to the $B_D$ value calculated on all of the axes; and additional indices obtained based on the $L_D$ index and/or the $B_D$ index.

12. The device according to claim 1, wherein the processor is programmed to perform an identification, quantification, and comparative assessment of a motor state similar to bradykinesia by determining whether the frequency content of each axis has a majority of frequencies comprised in an interval between 0.5 and 3 Hz, and by performing the following steps:

subdividing the entire monitoring sequence into the time sub-intervals and computing the spectral density ($S_x$, $S_y$ and $S_z$) for each single axis of the multi-axial measurement system and in each time sub-interval of the monitoring sequence;

performing a computation, for individual time sub-intervals and for each axis, of $E_{Bx}$, $E_{By}$ and $E_{Bz}$ parameters by integrating the spectral density densities $S_x$, $S_y$ and $S_z$ over a characteristic frequency range;

computing a $B_B=1/E_B$ index, where $E_B$ is defined as a linear or non-linear combination of the $E_{Bx}$, $E_{By}$ and $E_{Bz}$ parameters, for all of the time sub-intervals;

identifying a possible bradykinesia by evaluating the sub-intervals for which a $B_B$ index value is higher than a threshold value;

quantifying the possible bradykinesia by evaluating a value of the $B_B$ index only when the possible bradykinesia is identified;

computing one or more numerical indices, including:

a $L_B$ index, a computation of which includes evaluating a total number of time sub-intervals of the monitoring sequence in which a motor state of bradykinesia has been identified;

a $B_B^{TOT}$ index, obtained by adding the value of all the $B_B$ indices relative to all the time sub-intervals of the monitoring sequence;

a $\overline{B_B}$ index, a computation of which includes calculating an average value of all of the $B_B$ values;

a $BL_B^{TOT}=L_B \cdot B_B^{TOT}$ index and a $\overline{BL_B^{TOT}}=L_B \cdot \overline{B_B}$ index;

a $BL_B$ index, obtained by multiplying the $BL_B^{TOT}$ index and/or the $\overline{BL_B^{TOT}}$ index by a coefficient;

$B_{Bx}=E_{Bx}$, $B_{By}=E_{By}$, e $B_{Bz}=E_{Bz}$ indexes, representative of a contribution provided by each axis to the $B_B$ value evaluated on all of the axes; and additional indices obtained based on the $L_B$ index and/or the $B_B$ index.

13. The device according to claim 1, wherein the device is a watch that may be worn on a wrist.

14. The device according to claim 1, further configured to be in communication with an external processing unit for identification, qualitative assessment and quantitative evaluation of motor states.

* * * * *